(12) United States Patent
Pan et al.

(10) Patent No.: US 11,932,653 B2
(45) Date of Patent: Mar. 19, 2024

(54) LYCORINE DERIVATIVE, AND PHARMACEUTICAL COMPOSITION AND USE THEREOF

(71) Applicants: SHANDONG DYNE MARINE BIOPHARMACEUTICAL CO., LTD, Shandong (CN); BEIJING DYNE HIGH-TECH PEDIATRIC PHARMACEUTICAL R&D INSTITUTE CO., LTD., Beijing (CN)

(72) Inventors: Xiandao Pan, Beijing (CN); Yajun Yang, Beijing (CN); Longying Shen, Beijing (JP); Wensheng Zheng, Beijing (CN); Shuwang He, Rongcheng (CN); Shiqiang Yan, Rongcheng (CN); Yajun Jing, Rongcheng (CN)

(73) Assignees: SHANDONG DYNE MARINE BIOPHARMACEUTICAL CO., LTD, Shandong (CN); BEIJING DYNE HIGH-TECH PEDIATRIC PHARMACEUTICAL R&D INSTITUTE CO., LTD., Shandong (CN)

( * ) Notice: Subject to any disclaimer, the term of this patent is extended or adjusted under 35 U.S.C. 154(b) by 697 days.

(21) Appl. No.: 17/056,533

(22) PCT Filed: Jul. 27, 2018

(86) PCT No.: PCT/CN2018/097678
§ 371 (c)(1),
(2) Date: Nov. 18, 2020

(87) PCT Pub. No.: WO2020/019357
PCT Pub. Date: Jan. 30, 2020

(65) Prior Publication Data
US 2021/0206777 A1 Jul. 8, 2021

(51) Int. Cl.
*C07D 491/16* (2006.01)
*A61P 31/14* (2006.01)

(52) U.S. Cl.
CPC ............ *C07D 491/16* (2013.01); *A61P 31/14* (2018.01)

(58) Field of Classification Search
CPC .................................................. C07D 491/16
See application file for complete search history.

(56) References Cited

PUBLICATIONS

Li et al. "Identification of natural compounds with antiviral activities against SARS-associated coronavirus;" Antiviral Res; 2005; pp. 18-23; vol. 67, No. 1.

Wang et al.; "Anti-Dengue-Virus Activity and Structure-Activity Relationship Studies of Lycorine Derivatives;" ChemMedChem; 2014; pp. 1522-1533; vol. 9, No. 7.

Zou et al.; "A single-amino acid substitution in West Nile virus 2K peptide between NS4A and NS4B confers resistance to lycorine, a flavivirus inhibitor;" Virology; 2009; pp. 242-252; vol. 384, No. 1.

Gabrielsen et al; "Antiviral (RNA)activity of selected amaryllidaceae isoquinoline constituents and synthesis of related substances;" Journal of Natural Products; 1992; pp. 1569-1581; vol. 55, No. 11.

Szlavik et al.; "Alkaloids from Leucojum vernum and antiretroviral activity of amaryllidaceae alkaloids;" Planta Med; 2004; pp. 871-873; vol. 70, No. 9.

Renard-Nozaki et al.; Effect of alkaloids isolated from amaryllidaceae on herpes simples virus; Res Virol; 1989; pp. 115-128; vol. 140, No. 2.

Hwang et al.; "Rapid identification of inhibitors that interfere with poliovirus replication using a cell-based assay;" Antiviral Res.; 2008; pp. 232-236; vol. 77, No. 3.

Vrijsen et al.; lycorine: a eukaryotic termination inhibitor; J. Biol. Chem; 1986; 505-507; vol. 261, No. 2.

Liu et al.; Lycorine reduced mortality of human enterovirus 71-infected mice by inhibiting virus replication; Virology Journal; 2011; pp. 483-491; vol. 8, No. 1.

He et al.; "Amaryllidaceae alkaloids inhibit nuclear-to cytoplasmic export of ribonucleoprotein (RNP) complex of highly pathogenic avian influenza virus H5N1;" Influenza and Other Respiratory Viruses; 2013; pp. 922-931; vol. 7, No. 6.

Chen et al.; "Evaluation of anti-HCV activity and SAR study of (+)-lycoricidine through targeting of host heat-stress cognate 70 (Hsc70);" Bioorg Med Chem Lett; 2013; pp. 2679-2682; vol. 23, No. 9.

(Continued)

*Primary Examiner* — Shawquia Jackson
(74) *Attorney, Agent, or Firm* — Oliff PLC

(57) ABSTRACT

The present invention relates to the technical field of medicine, and particularly to a lycorine derivative of Formula (I), and a pharmaceutically acceptable salt, a preparation method, a pharmaceutical composition and use thereof. The lycorine derivative has obvious antiviral activity and is useful in the treatment of viral diseases such as hand-foot-mouth disease.

10 Claims, 1 Drawing Sheet

(56) References Cited

PUBLICATIONS

Wang; Synthesis and Biological Activity of Novel Lycorine Derivatives and Direct Aldol Reaction as Novel Bioorthogonal Reaction and Application in Site-Specific Modification of Protein; China Doctoral Dissertation Full-Text Database, Engineering Science & Technology I; 2015; pp. 3, 27 and 33-35; No. 7.

May 6, 2019 Search Report issued in International Patent Application No. PCT/CN2018/097678.

May 6, 2019 Written Opinion of the International Searching Authority issued in International Patent Application No. PCT/CN2018/097678.

LYCORINE DERIVATIVE, AND PHARMACEUTICAL COMPOSITION AND USE THEREOF

BACKGROUND

Technical Field

The present invention relates to the technical field of medicine, and particularly to a new lycorine derivative, a pharmaceutical composition including the lycorine derivative, and use thereof in the preparation of antiviral drugs.

Related Art

Lycorine is an alkaloid initially isolated from the scales of the traditional Chinese medicine Lycoris radiata Herb by Kota Morishima, a Japanese. Biological activity research shows that lycorine and its derivatives have various effects such as antiviral, anti-inflammatory, anti-tumor, anti-parasitic, acetylcholinesterase inhibition and cardiovascular protection effects.

Lycorine has antiviral activity against various RNA and DNA viruses. A study by Gabrielsen B et al. showed that lycorine exhibits an in-vitro inhibitory activity on various viruses such as Japanese encephalitis virus, yellow fever virus, and dengue virus. Lycorine also has an inhibitory effect on poliovirus, herpes virus, and Coxsackievirus B2. The degree of inhibition depends on the concentration, and the mechanism of antiviral action is related to the inhibition of DNA polymerase. Some studies believe that the effect of lycorine in delaying the virus growth and reducing the total number of viruses produced is associated with blocking the viral protein synthesis. In recent years, further studies on the antiviral effect of lycorine were conducted by the scholars in China and other countries, which showed that lycorine has an obvious inhibitory effect on HIV-1 virus replication. Lycorine is effective in inhibiting human severe acute respiratory syndrome (SARS)-associated coronavirus (SARS-CoV), but the mechanism of action is unclear and needs further study. A preliminary study on the activity of lycorine against hand-foot-and-mouth disease causing virus (EV71) was carried out by the present inventors, which showed that lycorine has good anti-EV71 activity in vitro and in vivo, and that lycorine can inhibit the 3D polymerase of the EV71 virus. Based on the previous research results, the present invention focuses on structural modification at position 1 of lycorine, and finds that such compounds have good antiviral activity.

REFERENCES

1 Li S Y, Chen C, Zhang H Q, et al. Identification of natural compounds with antiviral activities against SARS-associated coronavirus [J]. Antiviral Res., 2005, 67(1):18-23
2 Wang P, Li L F, Wang Q Y, et al. Anti-Dengue-Virus Activity and Structure-Activity Relationship Studies of Lycorine Derivatives [J]. ChemMedChem, 2014, 9(7): 1522-1533
3 Zou G, Basagoiti F P, Zhang B, et al. A single-amino acid substitution in West Nile virus 2K peptide between NS4A and NS4B confers resistance to lycorine, a flavivirus inhibitor [J]. Virology, 2009, 384 (1): 242-252
4 Gabrielsen B, Monath T P, Huggins J W, et al. Antiviral (RNA)activity of selected amaryllidaceaeisoquinoline constituents and synthesis of related substances [J]. Journal of Natural Products, 1992, 55(11):1569-1581
5 Szlavik L, Gyuris A, Minarovits J, et al. Alkaloids from Leucojumvernum and antiretroviral activity of amaryllidaceae alkaloids [J]. Planta Med, 2004, 70(9): 871-873
6 Nozaki J R, Kim T, Imakura Y, et al. Effect of alkaloids isolated from amaryllidaceae on herpes simples virus [J]. Res Virol, 1989, 140(2):115-128
7 Hwang Y C, Chu J H, Yang P L, et al. Rapid identification of inhibitors thatinterfere with poliovirus replication using a cell-based assay [J]. Antiviral Res. 2008, 77(3): 232-236
8 Vrijsen, R., VandenBerghe, D., Vlierinck, A., et al. A lycorine: a eukaryotic termination inhibitor [J]. J. Biol. Chem, 1986, 261(2): 505-507
9 Liu J N, Yang Y J, Xu Y F, et al. Lycorine reduced mortality of human enterovirus 71-infected mice by inhibiting virus replication [J]. Virology Journal, 2011, 8(1): 483-491
10 He J, Qi W B, Wang L, et al. Amaryllidaceae alkaloids inhibit nuclear-to cytoplasmic export of ribonucleoprotein (RNP) complex of highly pathogenic avian influenza virus H5N1[J]. Influenza and Other Respiratory Viruses, 2013, 7(6): 922-931
11 Chen D Z, Jiang J D, Zhang K Q, et al. Evaluation of anti-HCV activity and SAR study of (+)-lycoricidine through targeting of host heat-stress cognate 70 (Hsc70) [J]. Bioorg Med ChemLett, 2013, 23(9):2679-2682

SUMMARY

In view of the technical problems above, the present invention provides a lycorine derivative, and a pharmaceutically acceptable salt, a pharmaceutical composition and use thereof in the preparation of antiviral drugs.

To solve the technical problems of the present invention, the present invention provides the following technical solutions:

In a first aspect of the technical solution of the present invention, a lycorine derivative of General Formula (I), and a pharmaceutically acceptable salt thereof are provided:

General Formula (I)

where X is O, S or $CH_2$; n=0, 1, 2, 3, 4, or 5; Ar is a C6-10 aromatic ring or a C3-10 heteroaromatic ring; R is optionally mono- or multi-substituted, and R is independently selected from hydrogen, halogen, nitro, amino, hydroxy, C1-6 alkyl, C1-6 alkoxy, C1-6 alkylamino, C6-10 aryl, C1-6 alkynyl, C1-6 alkenyl, C3-6 cycloalkyl, C3-6 heterocycloalkyl, C1-6 alkylacyl, and C6-10 arylacyl.

Preferably, Ar is selected from phenyl, naphthyl, pyrimidinyl, pyridinyl, furyl, thienyl, pyrrolyl, isoxazolyl, isothiazolyl, pyrazolyl, oxazolyl, thiazolyl, imidazolyl, pyridazinyl, pyrazinyl, benzofuryl, benzothienyl, indolyl, quinolinyl, isoquinolinyl, purinyl, benzoxazolyl, benzothiazolyl. Preferably, R is selected from hydrogen, F, Cl, Br, I, nitro, amino, hydroxyl, C1-4 alkyl, C1-4 alkoxy, C1-4 alkylamino, phenyl, C1-4 alkynyl, and C1-4 alkenyl. The occurrence of substitution with the substituent R on the phenyl group is at the para, meta, or ortho position; and R is optionally mono-substituted, di-substituted or multi-substituted.

Most preferably, the lycorine derivative and pharmaceutically acceptable salt are selected from the group consisting of:

(1)
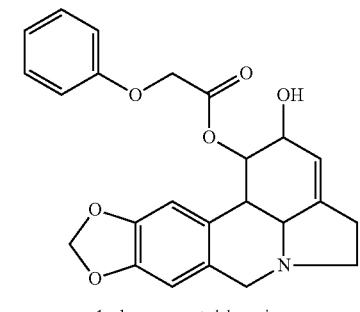
1-phenoxyacetyl-lycorine (2)
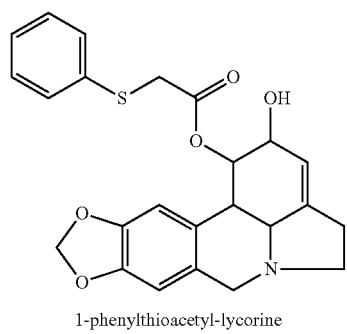
1-phenylthioacetyl-lycorine (3)
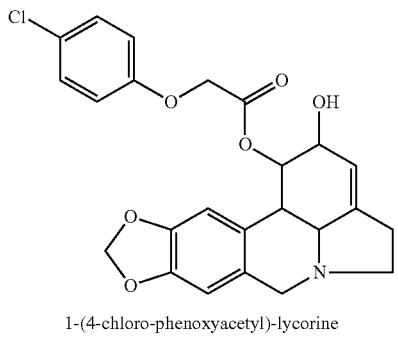
1-(4-chloro-phenoxyacetyl)-lycorine (4)
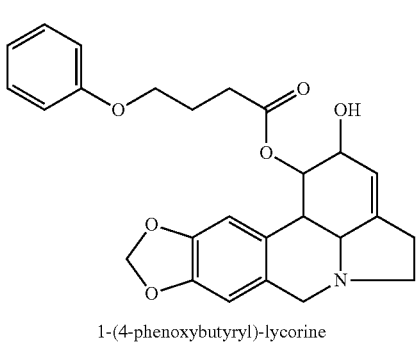
1-(4-phenoxybutyryl)-lycorine -continued (5)
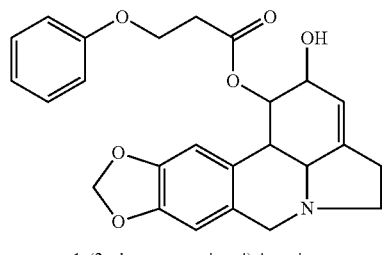
1-(3-phenoxypropionyl)-lycorine (6)
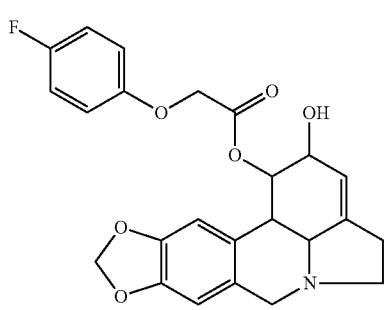
1-(4-fluoro-phenoxyacetyl)-lycorine (7)
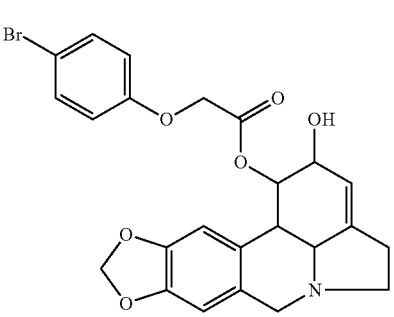
1-(4-bromo-phenoxyacetyl)-lycorine (8)
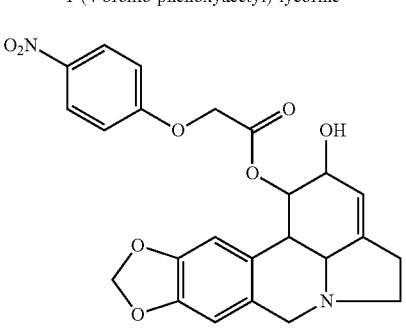
1-(4-nitro-phenoxyacetyl)-lycorine (9)
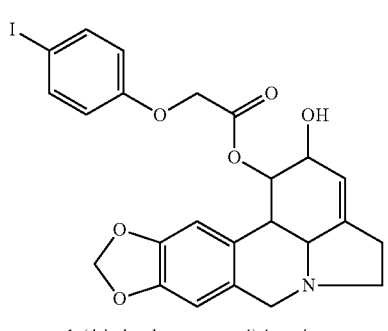
1-(4-iodo-phenoxyacetyl)-lycorine

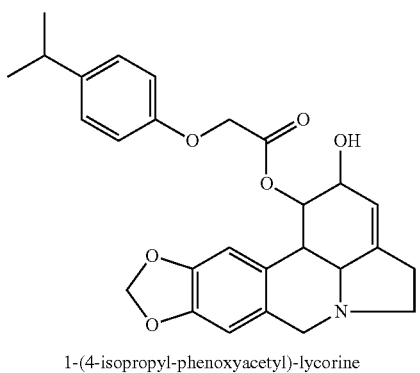
1-(4-isopropyl-phenoxyacetyl)-lycorine (10)
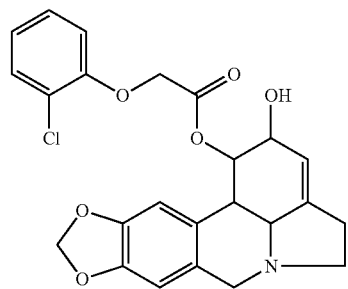
1-(2-chloro-phenoxyacetyl)-lycorine (14)
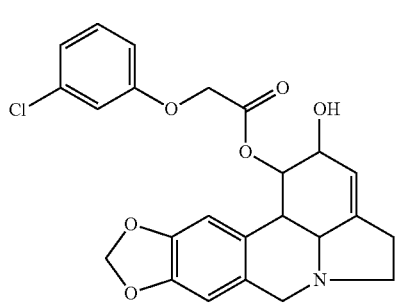
1-(3-chloro-phenoxyacetyl)-lycorine (15)
1-(4-chloro-phenylthioacetyl)-lycorine (11)
1-(4-methylphenoxyacetyl)-lycorine (12)
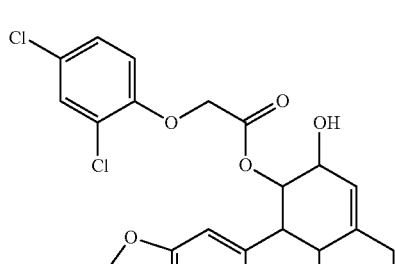
1-(2,4-dichloro-phenoxyacetyl)-lycorine (16)
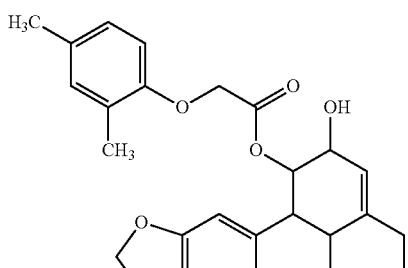
1-(2,4-dimethyl-phenoxyacetyl)-lycorine (13)
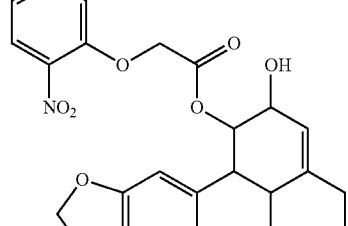
1-(4-nitro-phenoxyacetyl)-lycorine (17)

(18)
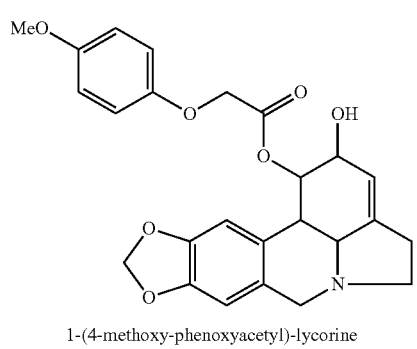
1-(4-methoxy-phenoxyacetyl)-lycorine
(19)
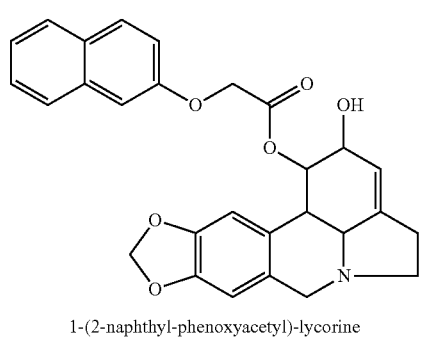
1-(2-naphthyl-phenoxyacetyl)-lycorine
(20)
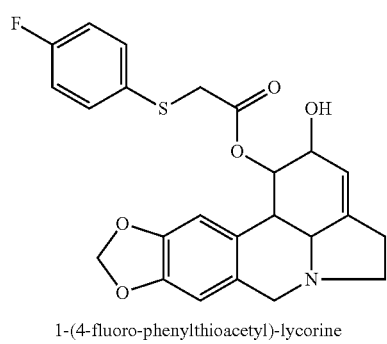
1-(4-fluoro-phenylthioacetyl)-lycorine
(21)
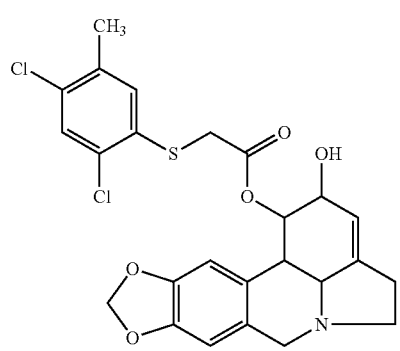
1-(2,4-dichloro-5-methyl-phenylthioacetyl)-lycorine
(22)
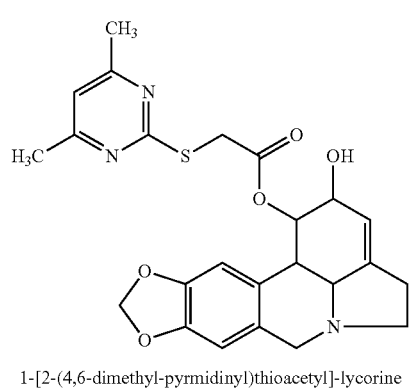
1-[2-(4,6-dimethyl-pyrmidinyl)thioacetyl]-lycorine
(23)
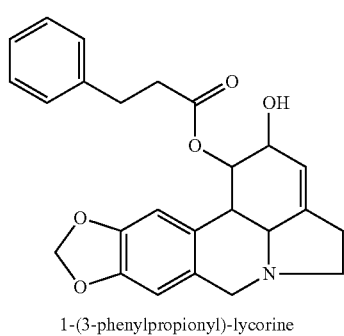
1-(3-phenylpropionyl)-lycorine
(24)
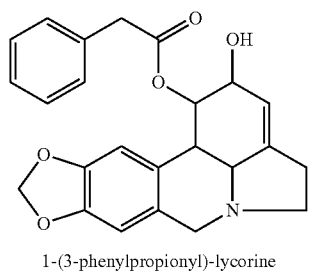
1-(3-phenylpropionyl)-lycorine
(25)
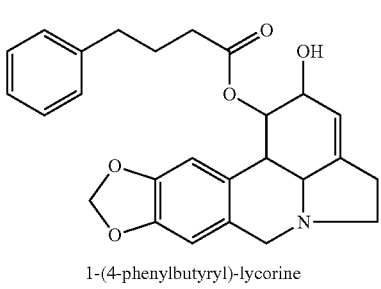
1-(4-phenylbutyryl)-lycorine
(26)
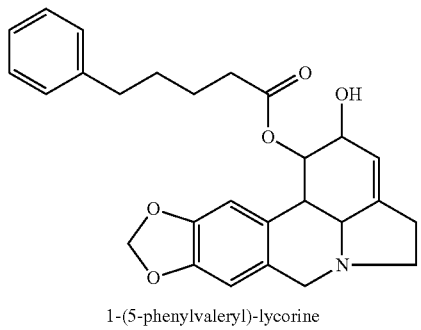
1-(5-phenylvaleryl)-lycorine

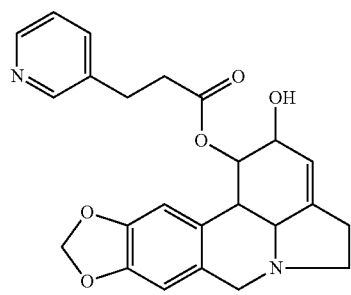

1-[3-(2-pyridinyl)propionyl]-lycorine (27)

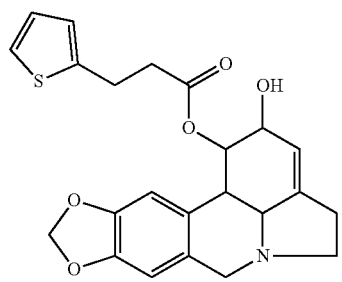

1-[3-(2-thienyl)propionyl]-lycorine (32)

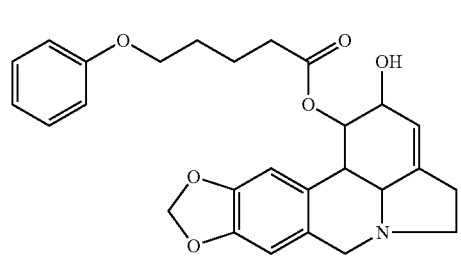

1-(5-phenoxyvaleryl)-lycorine (28)

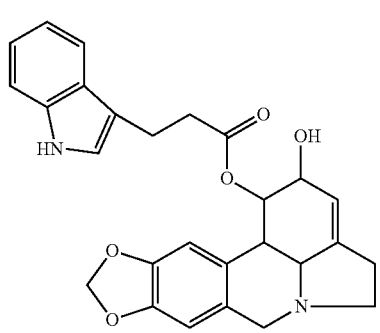

1-[3-(3-indolyl)propionyl]-lycorine (33)

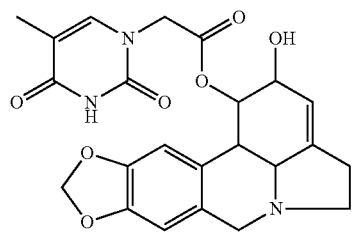

1-(1-thymineacetyl)-lycorine (29)

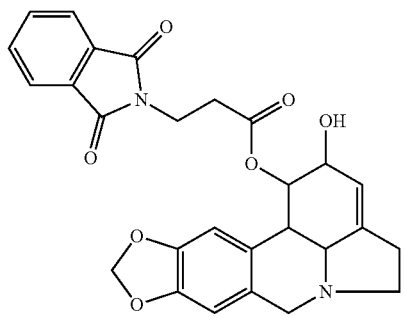

1-(3-phthalimidopropionyl)-lycorine (30)

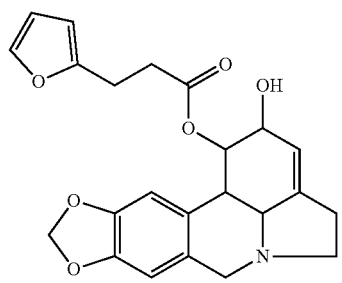

1-[3-(2-furyl)propionyl]-lycorine (31)

In a second aspect of the technical solution of the present invention, a method for preparing the compound according to the first aspect is provided, which includes Reaction Formula (I):

Reaction Formula (I)

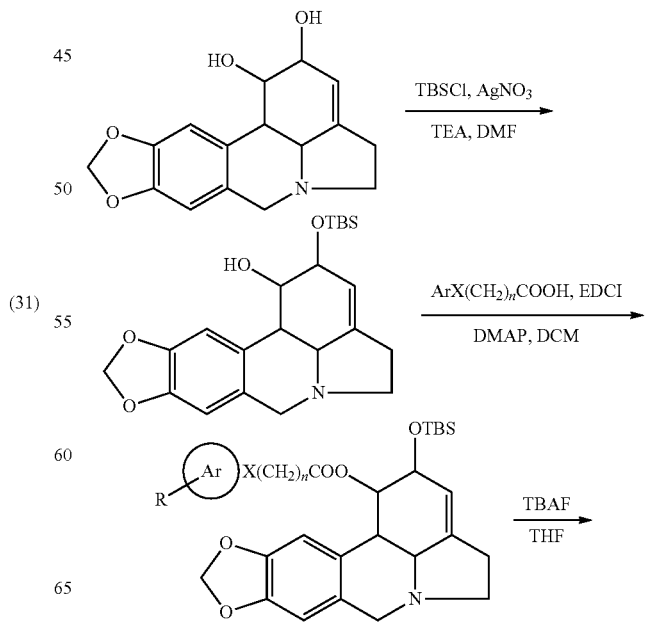

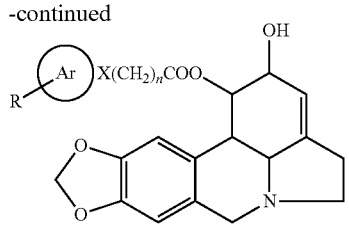

selectively protecting the hydroxyl group at position 2 of lycorine with silane, then reacting the hydroxyl group at position 1 with various acids, and finally removing the silane at position 2 in the presence of tetrabutylammonium fluoride (TBAF).

The compound of the present invention contains a basic group in the molecule, and can be converted into a pharmaceutically acceptable salt by acid treatment as recognized in the art. Examples of such salts include salts with inorganic acid, such as hydrochloride, hydrobromide, sulfate or hydrosulfate, nitrate, phosphate or hydrophosphate, and salts with organic acid, such as formate, acetate, benzoate, succinate, fumarate, maleate, lactate, citrate, tartrate, succinate, gluconate, methanesulfonate, benzenesulfonate, or p-toluenesulfonate.

In a third aspect of the technical solution of the present invention, a pharmaceutical composition is provided, which includes the lycorine derivative or a pharmaceutically acceptable salt according to the first aspect of the present invention and a pharmaceutically acceptable carrier or excipient.

The compound of the present invention can be administered orally, for example, in the form of capsules, tablets, powders, granules, syrups or similar dosage forms, or parenterally by in the form of injections, ointment, suppository or similar dosage forms. These pharmaceutical preparations can be produced in a conventional manner by using adjuvants well known in the art, such as binders, excipients, stabilizers, disintegrants, flavoring agents, and lubricants, etc. The dosage varies with the symptoms, the age of the patient, the nature and severity of the disease or disorder, and the route and mode of administration. For oral administration to adult patients, the compound of the present invention is normally administered at a total daily dosage of 1 to 1000 mg, and preferably 5 to 500 mg, either in a single dose or in divided doses, for example, twice or three times a day. For intravenous injections, a dosage of 0.1 to 100 mg, and preferably 0.5 to 50 mg, can be administered in a single dose to three divided doses a day.

In a fourth aspect of the technical solution of the present invention, the use of the lycorine derivative or a pharmaceutically acceptable salt thereof according to the first aspect or the pharmaceutical composition according to the third aspect in the preparation of antiviral drugs is provided, where the viruses include hand-foot-and-mouth disease causing viruses EV71 and CAV16.

Beneficial Technical Effect

The present invention focuses on providing a lycorine derivative of General Formula (I), obtained mainly by introducing various substituents to the hydroxyl group at position 1 of lycorine. Preliminary activity screening shows that such derivatives have higher antiviral activity, lower toxicity, and increased selectivity index, compared with lycorine. This indicates that such derivatives have better anti-virus prospects.

DETAILED DESCRIPTION

Figure 1:
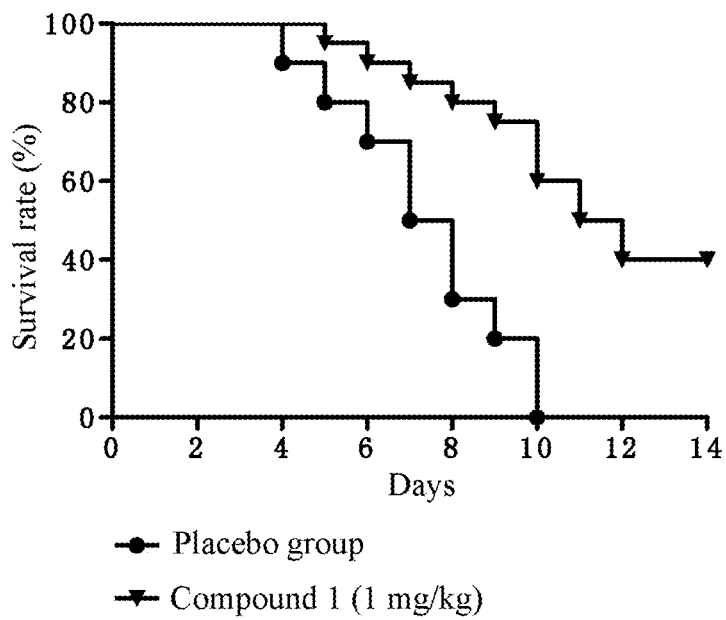
FIG. 1 shows the survival rate of EV71-infected mice treated with Compound 1.

Abbreviations:
DMF: N,N-dimethylformamide
DMAP: 4-dimethylaminopyridinyl
EDCI: 1-ethyl-(3-dimethylaminopropyl)carbodiimide hydrochloride
THF: tetrahydrofuran
TBSCl: tert-Butyldimethylsilyl chloride
TBAF: tetrabutylammonium fluoride The present invention discloses a lycorine derivative, or its salt, solvate, or prodrug, a pharmaceutical composition including the lycorine derivatives, or its salt, solvate, or prodrug, and use thereof. The process parameters can be suitably improved by those skilled in the art based on the disclosure herein. In particular, it should be noted that similar substitutions and modifications will readily occur to those skilled in the art, and are all embraced in the present invention. The method and use of the present invention have been described in conjunction with preferred embodiments, and it is obvious that the technology of the present invention can be implemented and used by changing or appropriately modifying and combining the method and use described herein by those skilled in the art without departing from the disclosure, spirit, and scope of the present invention.

Hereinafter, the present invention is further described by way of examples.

Example 1: 1-phenoxyacetyl-lycorine (1)

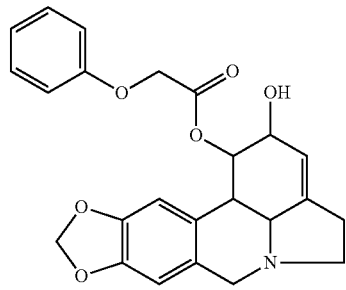 [SMILES: O=C(CSc1ccccc1)OC1C(O)C=C2CCN3Cc4cc5c(cc4C1C23)OCO5]

1-a: Lycorine (1.0 mmol), TBSCl (2.0 mmol), AgNO$_3$ (4.0 mmol), TEF (4.0 mmol), and DMF (15 ml) were fed to a 50 ml reaction flask, and stirred at room temperature in the dark until no raw materials remained. After filtration, the filtrate was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated to obtain 2-TBS-lycorine.

1-b: 2-TBS-lycorine, phenoxyacetic acid (1.0 mmol), EDCI (1.2 mmol), DMAP (0.1 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

1-c: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (53.4%). $^1$H NMR (400M, CDCl$_3$): δ 7.16-7.12 (m, 2H), 6.93-6.89 (m, 1H), 6.68-6.66 (m, 3H), 6.53 (s, 1H), 5.93 (d, J=8.0 Hz, 2H), 5.75 (s, 1H), 5.51 (s, 1H), 4.51 (s, 2H), 4.21 (s, 1H), 4.08 (d, J=16 Hz, 1H), 3.35-3.30 (m, 2H), 2.85 (d, J=8.0 Hz, 1H), 2.59 (m, 2H), 2.52 (d, J=8.0 Hz, 1H), 2.27 (d, J=20.0 and 8.0 Hz, 1H).

Example 2: 1-phenylthioacetyl-lycorine (2)

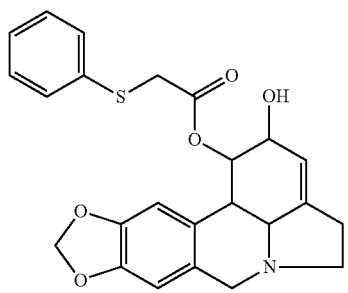

2-a: 2-TBS-lycorine (1.0 mmol), phenylthioacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

2-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (32.0%). $^1$H NMR (400M, CDCl$_3$): δ 7.18-7.17 (m, 5H), 6.66 (s, 1H), 6.54 (s, 1H), 5.90 (s, 2H), 5.64 (s, 1H), 5.49 (s, 1H), 4.13-4.09 (m, 2H), 3.51 (s, 2H), 3.45 (d, J=16.0 Hz, 1H), 3.35-3.33 (m, 1H), 2.86 (d, J=8.0 Hz, 1H), 2.63-2.60 (m, 3H), 2.37-2.36 (m, 1H).

Example 3: 1-(4-chloro-phenoxyacetyl)-lycorine (3)

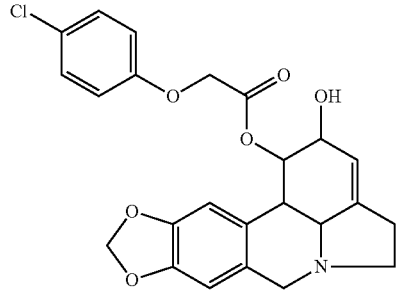 [SMILES: O=C(COc1ccc(Cl)cc1)OC1C(O)C=C2CCN3Cc4cc5c(cc4C1C23)OCO5]

3-a: 2-TBS-lycorine (1.0 mmol), 4-chloro-phenoxyacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

3-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (84.1%). $^1$H NMR (400M, CDCl$_3$): δ 7.08-7.04 (m, 2H), 6.66 (s, 1H), 6.58-6.54 (m, 3H), 6.00 (d, J=4.0 Hz, 1H), 5.94 (d, J=4.0 Hz, 1H), 5.76 (s, 1H), 5.52 (s, 1H), 4.52 (s, 2H), 4.20 (s, 1H), 4.10 (d, J=12.0 Hz, 1H), 3.36-3.28 (m, 2H), 2.85 (d, J=12.0 Hz, 1H), 2.59 (m, 2H), 2.41 (d, J=8.0 Hz, 1H), 2.27 (d, J=20.0 and 8.0 Hz, 1H).

Example 4: 1-(4-phenoxybutyryl)-lycorine (4)

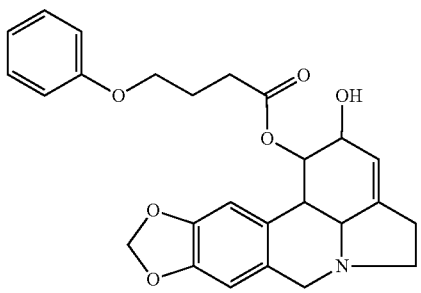 [SMILES: O=C(CCCOc1ccccc1)OC1C(O)C=C2CCN3Cc4cc5c(cc4C1C23)OCO5]

4-a: 2-TBS-lycorine (1.0 mmol), 4-phenoxybutanoic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

4-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a white solid (22.3%). $^1$H NMR (400M, CDCl$_3$): δ 7.25-7.22 (m, 2H), 6.92 (t, J=8.0 Hz, 1H), 6.78 (d, J=8.0 Hz, 1H), 6.70 (s, 1H), 6.53 (s, 1H), 5.88 (d, 1H), 5.83 (d, 1H), 5.68 (s, 1H), 5.53 (s, 1H), 4.21 (s, 2H), 4.12 (d, J=16.0 Hz, 1H), 3.80 (m, 2H), 3.45 (d, J=16.0 Hz, 1H), 3.36-3.32 (m, 2H), 2.87 (d, J=8.0 Hz, 1H), 2.71 (d, J=8.0 Hz, 1H), 2.62-2.61 (m, 2H), 2.43-2.33 (m, 3H), 2.00-1.94 (m, 2H).

Example 5: 1-(3-phenoxypropionyl)-lycorine (5)

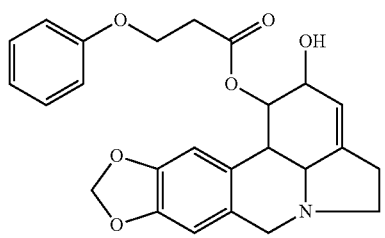 [SMILES: O=C(CCOc1ccccc1)OC1C(O)C=C2CCN3Cc4cc5c(cc4C1C23)OCO5]

5-a: 2-TBS-lycorine (1.0 mmol), 3-phenoxypropanoic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

5-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (11.5%). $^1$H NMR (400M, CDCl$_3$): δ 7.23 (t, J=8.0 Hz, 2H), 6.92 (t, J=8.0 Hz, 1H), 6.72 (d, J=8.0 Hz, 1H), 6.66 (s, 1H), 6.52 (s, 1H), 5.88 (d, 1H), 5.84 (d, 1H), 5.67 (s, 1H), 5.52 (s, 1H), 4.22 (s, 2H), 4.13-4.01 (m, 3H), 3.41 (d, J=12.0 Hz, 1H), 3.34-3.30 (m, 1H), 2.87 (d, J=8.0 Hz, 1H), 2.71-2.66 (m, 3H), 2.64-2.58 (m, 2H), 2.31 (d, J=16.0 and 8.0 Hz, 1H).

Example 6: 1-(4-fluoro-phenoxyacetyl)-lycorine (6)

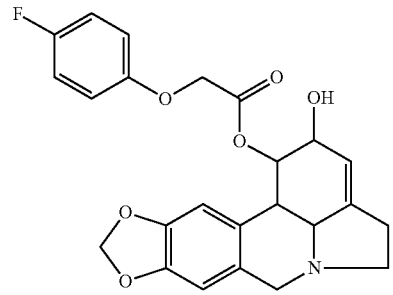 [SMILES: O=C(COc1ccc(F)cc1)OC1C(O)C=C2CCN3Cc4cc5c(cc4C1C23)OCO5]

6-a: 2-TBS-lycorine (1.0 mmol), 4-fluoro-phenoxyacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

6-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a white solid (45.6%). $^1$H NMR (400M, CDCl$_3$): δ 6.82-6.78 (m, 2H), 6.60-6.54 (m, 4H), 5.96 (s, 1H), 5.91 (s, 1H), 5.69 (s, 1H), 5.49 (s, 1H), 4.47 (s, 2H), 4.16 (s, 1H), 4.13-4.11 (m, 1H), 3.34-3.31 (m, 2H), 2.84 (d, J=8.0 Hz, 1H), 2.57 (m, 2H), 2.51 (d, J=12.0 Hz, 1H), 2.28 (d, J=20.0 and 8.0 Hz, 1H).

Example 7: 1-(4-bromo-phenoxyacetyl)-lycorine (7)

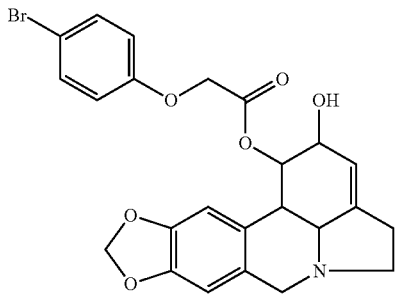

7-a: 2-TBS-lycorine (1.0 mmol), 4-bromo-phenoxyacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

7-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a white solid (48.6%). $^1$H NMR (400M, CDCl$_3$): δ 7.17 (d, J=8.0 Hz, 2H), 6.60 (s, 1H), 6.57 (s, 1H), 6.49 (d, J=8.0 Hz, 2H), 5.99 (s, 1H), 5.93 (s, 1H), 5.72 (s, 1H), 5.50 (s, 1H), 4.50 (s, 2H), 4.17 (s, 1H), 4.08 (d, J=8.0 Hz, 1H), 3.32-3.26 (m, 2H), 2.83 (d, J=12.0 Hz, 1H), 2.58 (s, 2H), 2.39 (s, 1H), 2.25 (s, 1H).

Example 8: 1-(4-nitro-phenoxyacetyl)-lycorine (8)

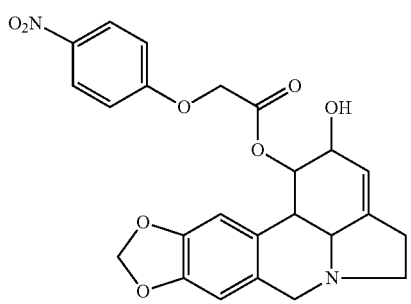 [SMILES: O=C(COc1ccc([N+](=O)[O-])cc1)OC1C(O)C=C2CCN3Cc4cc5c(cc4C1C23)OCO5]

8-a: 2-TBS-lycorine (1.0 mmol), 4-nitro-phenoxyacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

8-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (43.5%). $^1$H NMR (400M, CDCl$_3$): δ 7.02 (d, J=4.0 Hz, 2H), 6.67 (d, J=8.0 Hz, 2H), 6.55 (s, 1H), 6.51 (s, 1H), 6.02 (s, 1H), 5.92 (s, 1H), 5.71 (s, 1H), 5.51 (s, 1H), 4.63 (d, J=16.0 and 12.0 Hz, 2H), 4.19 (s, 1H), 4.08 (d, J=12.0 Hz, 1H), 3.33-3.31 (m, 1H), 3.24 (d, J=12.0 Hz, 1H), 2.83 (d, J=8.0 Hz, 1H), 2.59 (s, 2H), 2.43 (s, 1H), 2.24 (s, 1H).

Example 9: 1-(4-iodo-phenoxyacetyl)-lycorine (9)

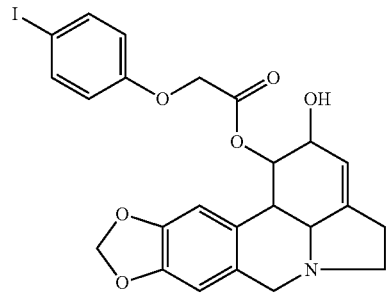 [SMILES: O=C(COc1ccc(I)cc1)OC1C(O)C=C2CCN3Cc4cc5c(cc4C1C23)OCO5]

9-a: 2-TBS-lycorine (1.0 mmol), 4-iodo-phenoxyacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

9-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a white solid (48.4%). $^1$H NMR (400M, CDCl$_3$): δ 7.34 (d, J=8.0 Hz, 2H), 6.59 (s, 2H), 6.37 (d, J=8.0 Hz, 2H), 5.99 (s, 1H), 5.93 (s, 1H), 5.70 (s, 1H), 5.49 (s, 1H), 4.49 (s, 2H), 4.15 (s, 1H), 4.08 (d, J=12.0 Hz, 1H), 3.33-3.23 (m, 2H), 2.81 (d, J=8.0 Hz, 1H), 2.57 (s, 2H), 2.36 (m, 1H), 2.24 (m, 1H).

Example 10: 1-(4-isopropyl-phenoxyacetyl)-lycorine (10)

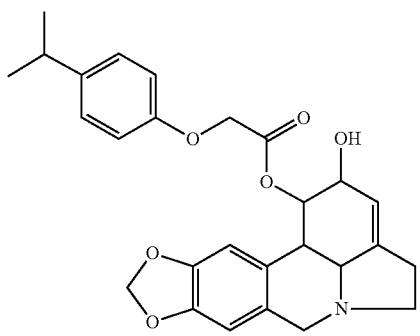 [SMILES: CC(C)c1ccc(OCC(=O)OC2C(O)C=C3CCN4Cc5cc6c(cc5C2C34)OCO6)cc1]

10-a: 2-TBS-lycorine (1.0 mmol), 4-isopropyl-phenoxyacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

10-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a white solid (59.8%). $^1$H NMR (400M, CDCl$_3$): δ 7.00 (d, J=8.0 Hz, 2H), 6.66 (s, 1H), 6.59 (d, J=8.0 Hz, 2H), 6.55 (s, 1H), 5.94 (s, 1H), 5.93 (s, 1H), 5.73 (s, 1H), 5.50 (s, 1H), 4.46 (s, 2H), 4.19 (s, 1H), 4.10 (d, J=8.0 Hz, 1H), 3.36-3.32 (m, 2H), 2.95-2.80 (m, 2H), 2.59 (m, 2H), 2.29 (s, 1H), 2.04 (s, 1H), 2.20 (d, 6H).

Example 11: 1-(4-chloro-phenylthioacetyl)-lycorine (11)

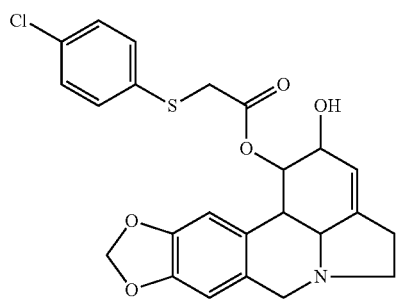

11-A: 2-TBS-lycorine (1.0 mmol), 4-chloro-phenylthio-acetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

11-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a white solid (66.4%). $^1$H NMR (400M, CDCl$_3$): δ 7.12 (d, J=8.0 Hz, 2H), 7.07 (d, J=4.0 Hz, 2H), 6.56 (s, 1H), 6.54 (s, 1H), 5.92 (s, 1H), 5.90 (s, 1H), 5.59 (s, 1H), 5.47 (s, 1H), 4.12-4.07 (m, 2H), 3.50-3.32 (m, 4H), 2.81 (d, J=8.0 Hz, 1H), 2.60 (s, 2H), 2.52 (m, 1H), 2.35-2.33 (m, 1H).

Example 12: 1-(4-methylphenoxyacetyl)-lycorine (12)

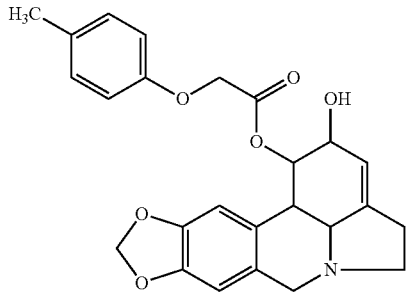 [SMILES: Cc1ccc(OCC(=O)OC2C(O)C=C3CCN4Cc5cc6c(cc5C2C34)OCO6)cc1]

12-a: 2-TBS-lycorine (1.0 mmol), 4-methylphenoxy-acetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

12-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (55.3%). $^1$H NMR (400M, CDCl$_3$): δ 6.91 (d, J=8.0 Hz, 2H), 6.62 (s, 1H), 6.55-6.63 (m, 3H), 5.94 (s, 1H), 5.92 (s, 1H), 5.71 (s, 1H), 5.50 (s, 1H), 4.48 (s, 2H), 4.16 (s, 1H), 4.08 (d, J=12.0 Hz, 1H), 3.32-3.31 (m, 2H), 2.84 (d, J=8.0 Hz, 1H), 2.58 (s, 2H), 2.51 (s, 1H), 2.28-2.27 (m, 1H), 2.24 (s, 3H).

Example 13: 1-(2,4-dimethyl-phenoxyacetyl)-lycorine (13)

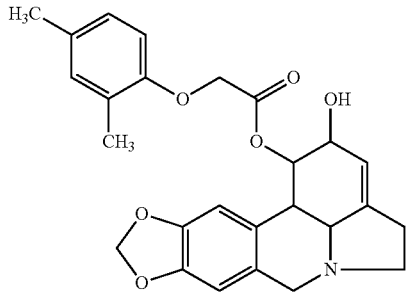 [SMILES: Cc1ccc(OCC(=O)OC2C(O)C=C3CCN4Cc5cc6c(cc5C2C34)OCO6)c(C)c1]

13-a: 2-TBS-lycorine (1.0 mmol), 2,4-dimethyl-phenoxy-acetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

13-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (57.2%). $^1$H NMR (400M, CDCl$_3$): δ 6.88 (s, 1H), 6.69-6.64 (m, 2H), 6.53 (s, 1H), 6.27 (d, J=8.0 Hz, 1H), 5.94 (s, 1H), 5.92 (s, 1H), 5.70 (s, 1H), 5.50 (s, 1H), 4.51 (s, 2H), 4.19 (s, 1H), 4.09 (d, J=12.0 Hz, 1H), 3.33 (s, 2H), 2.85 (d, J=8.0 Hz, 1H), 2.58 (s, 2H), 2.51 (s, 1H), 2.29 (s, 1H), 2.21 (s, 3H), 2.11 (s, 3H).

Example 14: 1-(2-chloro-phenoxyacetyl)-lycorine (14)

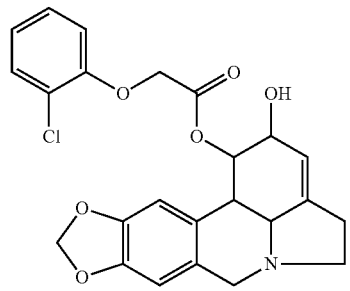 [SMILES: O=C(COc1ccccc1Cl)OC1C(O)C=C2CCN3Cc4cc5c(cc4C1C23)OCO5]

14-a: 2-TBS-lycorine (1.0 mmol), 2-chloro-phenoxyacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

14-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (64.3%). $^1$H NMR (400M, CDCl$_3$): δ 7.28 (m, 1H), 6.97-6.94 (m, 1H), 6.85-6.82 (m, 1H), 6.57 (s, 1H), 6.50-6.47 (m, 2H), 5.95 (s, 1H), 5.91 (s, 1H), 5.68 (s, 1H), 5.46 (s, 1H), 4.61 (d, 2H), 4.19 (s, 1H), 4.14-4.06 (m, 2H), 3.33-3.32 (m, 2H), 2.83 (d, J=8.0 Hz, 1H), 2.57 (s, 4H), 2.31 (s, 1H).

Example 15: 1-(3-chloro-phenoxyacetyl)-lycorine (15)

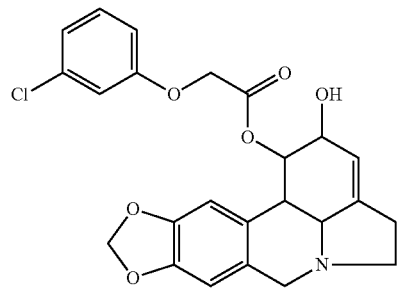 [SMILES: O=C(COc1cccc(Cl)c1)OC1C(O)C=C2CCN3Cc4cc5c(cc4C1C23)OCO5]

15-a: 3-TBS-lycorine (1.0 mmol), 2-chloro-phenoxyacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

15-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (56.4%). $^1$H NMR (400M, CDCl$_3$): δ 7.04-7.01 (m, 1H), 6.89-6.88 (m, 1H), 6.73 (s, 1H), 6.60 (s, 1H), 6.53-6.51 (m, 2H), 5.94 (s, 1H), 5.92 (s, 1H), 5.70 (s, 1H), 5.50 (s, 1H), 4.51 (s, 2H), 4.18 (s, 1H), 4.09 (d, J=8.0 Hz, 1H), 3.35-3.32 (m, 2H), 2.85 (d, J=8.0 Hz, 1H), 2.59 (s, 2H), 2.50 (s, 1H), 2.31 (s, 1H).

Example 16: 1-(2,4-dichloro-phenoxyacetyl)-lycorine (16)

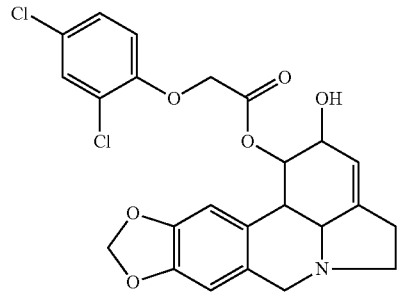 [SMILES: O=C(COc1ccc(Cl)cc1Cl)OC1C(O)C=C2CCN3Cc4cc5c(cc4C1C23)OCO5]

16-a: 2-TBS-lycorine (1.0 mmol), 2,4-dichloro-phenoxyacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

16-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (79.1%). $^1$H NMR (400M, CDCl$_3$): δ 7.28 (m, 1H), 6.86 (d, J=4.0 Hz, 1H), 6.57 (s, 1H), 6.54 (s, 1H), 6.37 (d, J=4.0 Hz, 1H), 5.99 (s, 1H), 5.92 (s, 1H), 5.69 (s, 1H), 5.49 (s, 1H), 4.61 (d, 2H), 4.16 (s, 1H), 4.08 (d, J=8.0 Hz, 1H), 3.34-3.32 (m, 2H), 2.83 (d, J=8.0 Hz, 1H), 2.59 (s, 2H), 2.47 (s, 1H), 2.30-2.29 (m, 1H).

Example 17: 1-(4-nitro-phenoxyacetyl)-lycorine (17)

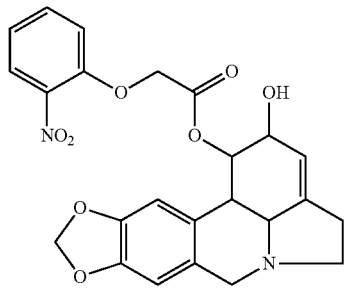 [SMILES: O=C(COc1ccccc1[N+](=O)[O-])OC1C(O)C=C2CCN3Cc4cc5c(cc4C1C23)OCO5]

17-a: 2-TBS-lycorine (1.0 mmol), 4-nitro-phenoxyacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

17-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a green solid (79.6%). $^1$H NMR (400M, CDCl$_3$): δ 7.73 (d, J=4.0 Hz, 1H), 7.24-7.23 (m, 1H), 6.98-6.96 (m, 1H), 6.61 (d, J=4.0 Hz, 1H), 6.54 (s, 1H), 6.48 (s, 1H), 5.97 (s, 1H), 5.90 (s, 1H), 5.67 (s, 1H), 5.46 (s, 1H), 4.69 (d, 2H), 4.12 (s, 1H), 4.06 (d, J=12.0 Hz, 1H), 3.32-3.30 (m, 2H), 2.81 (d, J=8.0 Hz, 1H), 2.57 (s, 2H), 2.50-2.49 (m, 1H), 2.35-2.33 (m, 1H).

Example 18: 1-(4-methoxy-phenoxyacetyl)-lycorine (18)

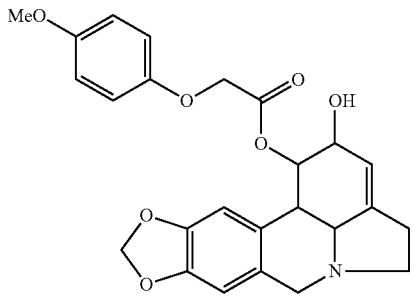 [SMILES: COc1ccc(OCC(=O)OC2C(O)C=C3CCN4Cc5cc6c(cc5C2C34)OCO6)cc1]

18-a: 2-TBS-lycorine (1.0 mmol), 4-methoxy-phenoxyacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

18-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (84.5%). $^1$H NMR (400M, CDCl$_3$): δ 6.67-6.58 (m, 5H), 6.53 (s, 1H), 5.94 (s, 1H), 5.91 (s, 1H), 5.71 (s, 1H), 5.50 (s, 1H), 4.46 (s, 2H), 4.18 (s, 1H), 4.09 (d, J=8.0 Hz, 1H), 3.73 (s, 3H), 3.36-3.31 (m, 2H), 2.84 (d, J=8.0 Hz, 1H), 2.59 (s, 2H), 2.55 (s, 1H), 2.29 (s, 1H).

Example 19: 1-(2-naphthyl-phenoxyacetyl)-lycorine (19)

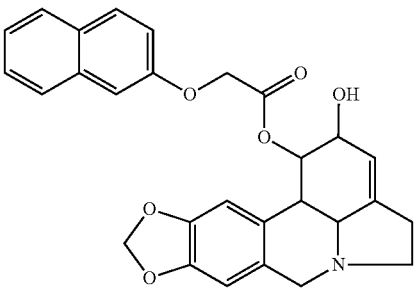 [SMILES: O=C(COc1ccc2ccccc2c1)OC1C(O)C=C2CCN3Cc4cc5c(cc4C1C23)OCO5]

19-A: 2-TBS-lycorine (1.0 mmol), 2-naphthyl-phenoxyacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

19-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (59.6%). $^1$H NMR (400M, CDCl$_3$): δ 7.73 (d, J=4.0 Hz, 1H), 7.65 (d, J=4.0 Hz, 1H), 7.49-7.47 (m, 1H), 7.42-7.39 (m, 1H), 7.35-7.32 (m, 1H), 7.06-7.04 (m, 1H), 6.78 (s, 1H), 6.63 (s, 1H), 6.38 (s, 1H), 5.88 (s, 1H), 5.87 (s, 1H), 5.73 (s, 1H), 5.46 (s, 1H), 4.66 (d, 2H), 4.20 (s, 1H), 3.95 (d, J=8.0 Hz, 1H), 3.25-3.22 (m, 1H), 3.05-3.02 (m, 1H), 2.80 (d, J=8.0 Hz, 1H), 2.52-2.36 (m, 3H), 2.10 (s, 1H).

Example 20: 1-(4-fluoro-phenylthioacetyl)-lycorine (20)

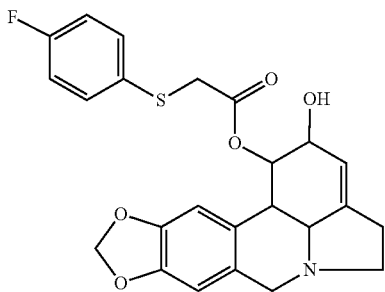 [SMILES: O=C(CSc1ccc(F)cc1)OC1C(O)C=C2CCN3Cc4cc5c(cc4C1C23)OCO5]

20-a: 2-TBS-lycorine (1.0 mmol), 4-fluoro-phenylthioacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

20-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (46.7%). $^1$H NMR (400M, CDCl$_3$): δ 7.18-7.15 (m, 2H), 689-6.85 (m, 2H), 6.56 (s, 1H), 6.54 (s, 1H), 5.91 (s, 1H), 5.89 (d, 1H), 5.58 (s, 1H), 5.46 (s, 1H), 4.13-4.06 (m, 2H), 3.47-3.31 (m, 4H), 2.81 (d, J=8.0 Hz, 1H), 2.57 (s, 2H), 2.54 (s, 1H), 2.35-2.31 (m, 1H).

Example 21: 1-(2,4-dichloro-5-methyl-phenylthio-acetyl)-lycorine (21)

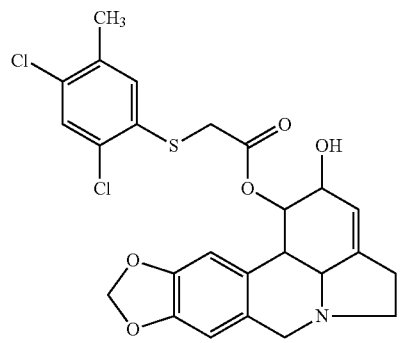 [SMILES: Cc1cc(SCC(=O)OC2C(O)C=C3CCN4Cc5cc6c(cc5C2C34)OCO6)c(Cl)cc1Cl]

21-a: 2-TBS-lycorine (1.0 mmol), 2,4-dichloro-5-methyl-phenylthioacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

21-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (82.7%). $^1$H NMR (400M, CDCl$_3$): δ 7.28 (s, 1H), 7.00 (s, 1H), 6.53 (s, 1H), 6.49 (s, 1H), 5.91 (d, 1H), 5.86 (d, 1H), 5.57 (s, 1H), 5.44 (s, 1H), 4.09-4.06 (m, 2H), 3.53 (d, J=12.0 Hz, 2H), 3.38-3.32 (m, 2H), 2.79 (d, J=12.0 Hz, 1H), 2.57-2.52 (m, 2H), 2.31-2.25 (m, 4H).

Example 22: 1-[2-(4,6-dimethyl-pyrimidinyl)thio-acetyl]-lycorine (22)

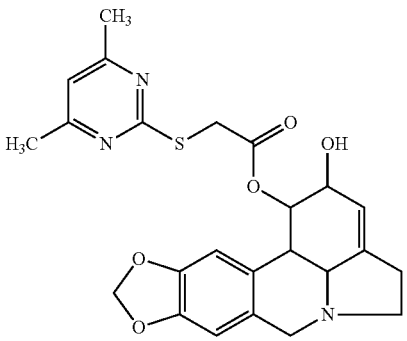 [SMILES: Cc1cc(C)nc(SCC(=O)OC2C(O)C=C3CCN4Cc5cc6c(cc5C2C34)OCO6)n1]

22-a: 2-TBS-lycorine (1.0 mmol), 2-(4,6-dimethyl-pyrimidinyl)thioacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

22-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (46.9%). $^1$H NMR (400M, CDCl$_3$): δ 6.63 (s, 1H), 6.56 (s, 1H), 6.50 (s, 1H), 5.91 (s, 1H), 5.88 (s, 1H), 5.56 (s, 1H), 5.46 (s, 1H), 4.18 (s, 1H), 4.08 (d, J=16.0 Hz, 1H), 3.85-3.70 (m, 2H), 3.41 (d, J=16.0 Hz, 1H), 3.32 (m, 1H), 2.81 (d, J=8.0 Hz, 1H), 2.79 (d, J=8.0 Hz, 1H), 2.56-2.55 (m, 2H), 2.35-2.31 (m, 7H).

Example 23: 1-(3-phenylpropionyl)-lycorine (23)

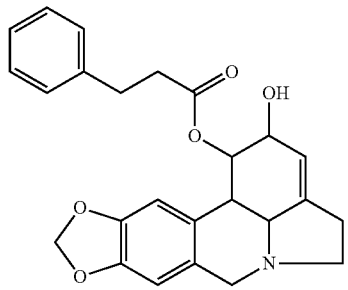 [SMILES: O=C(CCc1ccccc1)OC1C(O)C=C2CCN3Cc4cc5c(cc4C1C23)OCO5]

23-a: 2-TBS-lycorine (1.0 mmol), 3-phenylpropanoic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

23-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (23.9%). $^1$H NMR (400M, CDCl$_3$): δ 7.22-7.14 (m, 3H), 7.05 (d, J=8.0 Hz, 2H), 6.64 (s, 1H), 6.55 (s, 1H), 5.92 (d, J=4.0 Hz, 1H), 5.51 (s, 1H), 5.50 (s, 1H), 4.12 (d, J=12.0 Hz, 1H), 4.07 (s, 1H), 3.48 (d, J=16.0 Hz, 1H), 3.36-3.32 (m, 1H), 2.87 (d, J=8.0 Hz, 1H), 2.81 (t, J=8.0 Hz, 1H), 2.70 (d, J=12.0 Hz, 1H), 2.61-2.60 (m, 2H), 2.52 (t, J=8.0 Hz, 1H), 2.37 (d, J=20.0 and 8.0 Hz, 1H).

Example 24: 1-(3-phenylpropionyl)-lycorine (24)

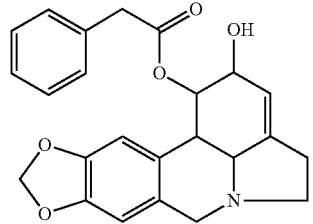 [SMILES: O=C(Cc1ccccc1)OC1C(O)C=C2CCN3Cc4cc5c(cc4C1C23)OCO5]

24-a: 2-TBS-lycorine (1.0 mmol), phenylacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

24-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (45.7%). $^1$H NMR (400M, CDCl$_3$): δ 7.16-7.14 (m, 3H), 7.01-6.99 (m, 2H), 6.59 (s, 1H), 6.53 (s, 1H), 5.90 (d, 1H), 5.62 (s, 1H), 5.51 (s, 1H), 4.17 (s, 1H), 4.11 (d, J=12 Hz, 1H), 3.48 (s, 2H), 3.42 (d, J=12 Hz, 1H), 3.35-3.34 (m, 1H), 2.82 (d, J=8 Hz, 1H), 2.63-2.61 (m, 3H), 2.33 (m, 1H).

Example 25: 1-(4-phenylbutyryl)-lycorine (25)

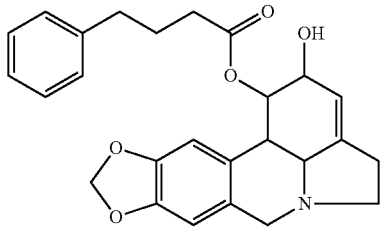 [SMILES: O=C(CCCc1ccccc1)OC1C(O)C=C2CCN3Cc4cc5c(cc4C1C23)OCO5]

25-a: 2-TBS-lycorine (1.0 mmol), 4-phenylbutanoic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

25-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (31.6%). $^1$H NMR (400M, CDCl$_3$): δ 7.23-7.15 (m, 3H), 6.98 (d, J=8 Hz, 2H), 6.72 (s, 1H), 6.56 (s, 1H), 5.88 (s, 1H), 5.79 (s, 1H), 5.68 (s, 1H), 5.55 (s, 1H), 4.19 (s, 1H), 4.16 (d, J=12 Hz, 1H), 3.51 (d, J=12 Hz, 1H), 3.37-3.36 (m, 1H), 2.88 (d, J=8 Hz, 1H), 2.75 (d, J=8 Hz, 1H), 2.64 (m, 2H), 2.48-2.37 (m, 4H), 2.20 (t J=8 Hz, 2H), 1.82-1.77 (m, 2H).

Example 26: 1-(5-phenylvaleryl)-lycorine (26)

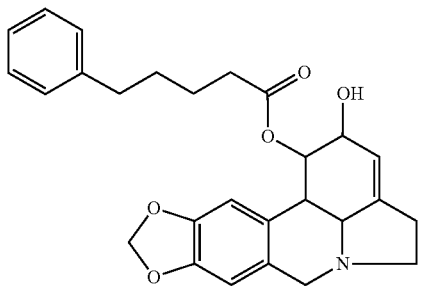

26-a: 2-TBS-lycorine (1.0 mmol), 5-phenylpentanoic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

26-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (28.7%). $^1$H NMR (400M, CDCl$_3$): δ 7.25-7.16 (m, 3H), 7.08 (d, J=8 Hz, 2H), 6.69 (s, 1H), 6.54 (s, 1H), 5.88 (s, 1H), 5.81 (s, 1H), 5.66 (s, 1H), 5.54 (s, 1H), 4.18 (s, 1H), 4.14 (d, J=12 Hz, 1H), 3.50 (d, J=12 Hz, 1H), 3.36-3.35 (m, 1H), 2.88 (d, J=8 Hz, 1H), 2.74 (d, J=8 Hz, 1H), 2.63 (m, 2H), 2.50-2.49 (m, 2H), 2.39 (q, J=8 Hz, 1H), 2.22-2.19 (m, 2H), 1.53-1.43 (m, 5H).

Example 27: 1-[3-(2-pyridinyl)propionyl]-lycorine (27)

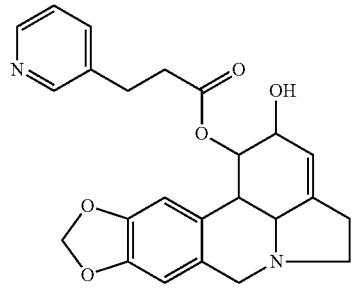 [SMILES: O=C(CCc1cccnc1)OC1C(O)C=C2CCN3Cc4cc5c(cc4C1C23)OCO5]

27-a: 2-TBS-lycorine (1.0 mmol), 3-(2-pyridinyl)propanoic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

27-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (34.0%). $^1$H NMR (400M, CDCl$_3$): δ 8.41 (d, J=4 Hz, 1H), 8.36 (s, 1H), 7.38 (d, J=8 Hz, 1H), 7.14-7.12 (m, 1H), 6.66 (s, 1H), 6.56 (s, 1H), 5.94 (s, 1H), 5.91 (s, 1H), 5.66 (s, 1H), 5.51 (s, 1H), 4.14-4.10 (m, 2H), 3.49 (d, J=12 Hz, 1H), 3.36-3.34 (m, 1H), 2.87-2.82 (m, 3H), 2.68-2.62 (m, 1H), 2.64 (m, 4H), 2.54 (t, J=8 Hz, 2H), 2.38 (m, 1H).

Example 28: 1-(5-phenoxyvaleryl)-lycorine (28)

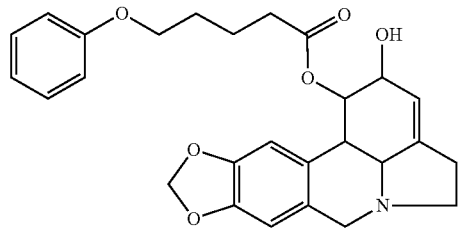 [SMILES: O=C(CCCCOc1ccccc1)OC1C(O)C=C2CCN3Cc4cc5c(cc4C1C23)OCO5]

28-a: 2-TBS-lycorine (1.0 mmol), 5-phenoxypentanoic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

28-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (22.7%). $^1$H NMR (400M, CDCl$_3$): δ 7.28-7.24 (m, 2H), 6.92 (t, J=8 Hz, 1H), 6.83-6.81 (m, 2H), 6.70 (s, 1H), 6.55 (s, 1H), 5.88 (s, 1H), 5.85 (s, 1H), 5.67 (s, 1H), 5.55 (s, 1H), 4.20 (s, 1H), 4.15 (d, J=12 Hz, 1H), 3.80 (t, J=4 Hz, 2H), 3.52 (d, J=12 Hz, 1H), 3.37-3.35 (m, 1H), 2.91 (d, J=8 Hz, 1H), 2.77 (d, J=8 Hz, 1H), 2.64 (m, 2H), 2.40-2.39 (m, 2H), 2.27 (t, J=4 Hz, 1H), 1.68 (m, 1H).

Example 29: 1-(1-thymineacetyl)-lycorine (29)

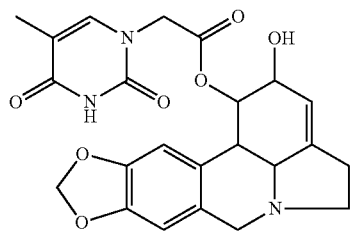 [SMILES: Cc1cn(CC(=O)OC2C(O)C=C3CCN4Cc5cc6c(cc5C2C34)OCO6)c(=O)[nH]c1=O]

29-a: 2-TBS-lycorine (1.0 mmol), 1-thymineacetic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

29-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (35.9%). $^1$H NMR (400M, CDCl$_3$): δ 9.18 (s, 1H), 6.72 (s, 1H), 6.67 (s, 1H), 6.57 (s, 1H), 5.96 (s, 1H), 5.91 (s, 1H), 5.70 (s, 1H), 5.53 (s, 1H), 4.34 (d, J=12 Hz, 1H), 4.24-4.08 (m, 3H), 3.44 (d, J=12 Hz, 1H), 3.39-3.37 (m, 1H), 2.98 (d, J=8 Hz, 1H), 2.62-2.61 (m, 3H), 2.36-2.32 (m, 1H).

Example 30: 1-(3-phthalimidopropionyl)-lycorine (30)

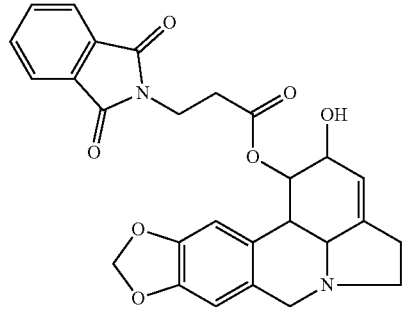 [SMILES: O=C(CCN1C(=O)c2ccccc2C1=O)OC1C(O)C=C2CCN3Cc4cc5c(cc4C1C23)OCO5]

30-a: 2-TBS-lycorine (1.0 mmol), 3-phthalimidopropanoic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

30-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (28.4%). $^1$H NMR (400M, CDCl$_3$): δ 7.82-7.80 (m, 2H), 7.72-7.70 (m, 2H), 6.67 (s, 1H), 6.51 (s, 1H), 5.90 (s, 1H), 5.89 (s, 1H), 5.63 (s, 1H), 5.49 (s, 1H), 4.22 (s, 1H), 4.13-4.08 (m, 2H), 3.91-3.84 (m, 2H), 3.45 (d, J=12 Hz, 1H), 3.32 (t, J=8 Hz, 1H), 2.84 (d, J=12 Hz, 1H), 2.69-2.54 (m, 4H), 2.32-2.29 (m, 1H).

Example 31: 1-[3-(2-furyl)propionyl]-lycorine (31)

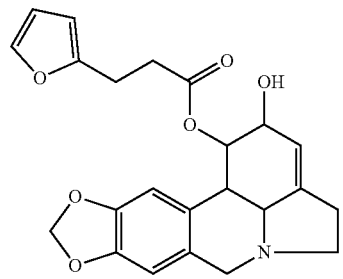

31-a: 2-TBS-lycorine (1.0 mmol), 3-(2-furyl)propanoic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

31-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (23.9%). $^1$H NMR (400M, CDCl$_3$): δ 7.22 (s, 1H), 6.67 (s, 1H), 6.56 (s, 1H), 6.19 (s, 1H), 5.92 (s, 1H), 5.91 (s, 1H), 5.84 (d, 1H), 5.64 (s, 1H), 5.52 (s, 1H), 4.15-4.12 (m, 2H), 3.50 (d, J=12 Hz, 1H), 3.37-3.33 (m, 1H), 2.86-2.82 (m, 3H), 2.71 (d, J=8 Hz, 1H), 2.62 (m, 2H), 2.55-2.52 (m, 2H), 2.40-2.35 (m, 1H).

Example 32: 1-[3-(2-thienyl)propionyl]-lycorine (32)

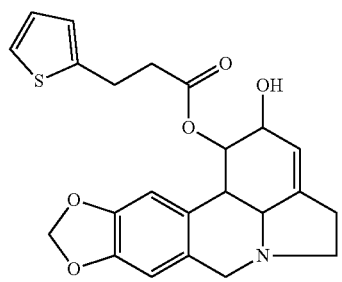 [SMILES: O=C(CCc1cccs1)OC1C(O)C=C2CCN3Cc4cc5c(cc4C1C23)OCO5]

32-a: 2-TBS-lycorine (1.0 mmol), 3-(2-thienyl)propanoic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

32-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (21.8%). $^1$H NMR (400M, CDCl$_3$): δ 7.06 (d, 1H), 6.83-6.82 (m, 1H), 6.66-6.65 (m, 2H), 6.56 (s, 1H), 5.92 (s, 1H), 5.91 (s, 1H), 5.66 (s, 1H), 5.51 (s, 1H), 4.15-4.12 (m, 2H), 3.49 (d, J=8 Hz, 1H), 3.36-3.34 (m, 1H), 3.02 (t, J=8 Hz, 2H), 2.85 (d, J=8 Hz, 1H), 2.70 (d, J=8 Hz, 1H), 2.62 (m, 2H), 2.57 (t, J=8 Hz, 2H), 2.38-2.36 (m, 1H).

Example 33: 1-[3-(3-indolyl)propionyl]-lycorine (33)

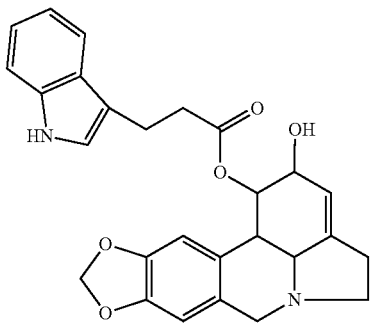 [SMILES: O=C(CCc1c[nH]c2ccccc12)OC1C(O)C=C2CCN3Cc4cc5c(cc4C1C23)OCO5]

33-a: 2-TBS-lycorine (1.0 mmol), 3-(3-indolyl)propanoic acid (1.2 mmol), EDCI (1.2 mmol), DMAP (0.12 mmol), and dichloromethane (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, and concentrated for use.

33-b: The product obtained in the above step, TBAF (2.0 mmol), and THF (15 ml) were fed to a 50 ml reaction flask, and stirred at room temperature until no raw materials remained. The reaction solution was transferred to a separatory funnel, and dichloromethane (50 ml) was added. The organic phase was washed respectively with saturated sodium bicarbonate solution, water, and saturated sodium chloride solution, dried over anhydrous sodium sulfate, concentrated, and separated by column chromatography to obtain a yellow solid (18.1%). $^1$H NMR (400M, CDCl$_3$): δ 7.92 (s, 1H), 7.48 (d, J=4 Hz, 1H), 7.30 (d, J=4 Hz, 1H), 7.16 (t, J=8 Hz, 1H), 7.06 (t, J=8 Hz, 1H), 6.77 (s, 1H), 6.66 (s, 1H), 6.53 (s, 1H), 5.90 (d, J=4 Hz, 1H), 5.61 (s, 1H), 5.46 (s, 1H), 4.12-4.07 (m, 2H), 3.40 (d, J=12 Hz, 1H), 3.32-3.29 (m, 1H), 2.95 (t, J=8 Hz, 1H), 2.81 (d, J=8 Hz, 1H), 2.63-2.56 (m, 6H), 2.30 (m, 1H).

PHARMACOLOGICAL EXPERIMENT

Experimental Example 1: In-Vitro Experiment of Various Compounds Against EV71 Virus RD cells were seeded into a 96-well plate (10$^4$ cells/well), and infected with 100× TCID$_{50}$ of EV71 viruses. After 2 hrs, various concentrations of the derivative were added. 48 hrs after administration, MTT was added, and the cell viability was measured on a microplate reader to calculate the EC$_{50}$. Uninfected cells were also given various concentrations of the derivative to determine the CC$_{50}$.

TABLE 1

In-vitro test results of compounds against EV71

| Compound | CC$_{50}$ (μM) | EC$_{50}$ (μM) | SI |
|---|---|---|---|
| 1 | 118.76 | 1.64 | 72.41 |
| 2 | 114.42 | 1.65 | 69.35 |
| 3 | 153.84 | 1.28 | 139.85 |

TABLE 1-continued

In-vitro test results of compounds against EV71

| Compound | $CC_{50}$ (μM) | $EC_{50}$ (μM) | SI |
|---|---|---|---|
| 4 | 149.51 | 1.76 | 84.84 |
| 5 | 134.02 | 1.45 | 92.43 |
| 6 | 131.19 | 1.27 | 103.30 |
| 7 | 103.43 | 1.47 | 70.36 |
| 8 | 105.38 | 1.23 | 85.67 |
| 9 | 99.64 | 1.84 | 54.15 |
| 10 | 101.25 | 1.67 | 60.63 |
| 11 | 130.52 | 1.46 | 89.40 |
| 12 | 134.22 | 1.53 | 87.73 |
| 13 | 148.71 | 1.56 | 95.33 |
| 14 | 145.24 | 1.63 | 89.10 |
| 15 | 151.56 | 1.73 | 87.61 |
| 16 | 129.86 | 1.71 | 75.94 |
| 17 | 156.25 | 1.71 | 91.37 |
| 18 | 161.12 | 1.65 | 97.65 |
| 19 | 163.41 | 1.97 | 82.94 |
| 23 | 128.52 | 1.73 | 74.28 |
| Lycorine | 104.52 | 2.26 | 46.24 |

Experimental Example 2: In-Vitro Experiment of Various Compounds Against Coxsackievirus Virus A16 (CAV16)

RD cells were seeded into a 96-well plate ($10^4$ cells/well), and infected with 100×$TCID_{50}$ of CAV16 viruses. After 2 hrs, various concentrations of the derivative were added. 48 hrs after administration, MTT was added, and the cell viability was measured on a microplate reader to calculate the $EC_{50}$. Uninfected cells were also given various concentrations of the derivative to determine the $CC_{50}$.

TABLE 2

In-vitro test results of compounds against CAV16

| Compound | $CC_{50}$ (μM) | $EC_{50}$ (μM) | SI |
|---|---|---|---|
| 1 | 118.76 | 1.19 | 99.80 |
| 2 | 114.42 | 0.57 | 200.73 |
| Lycorine | 104.52 | 1.57 | 66.57 |

Figure 2:
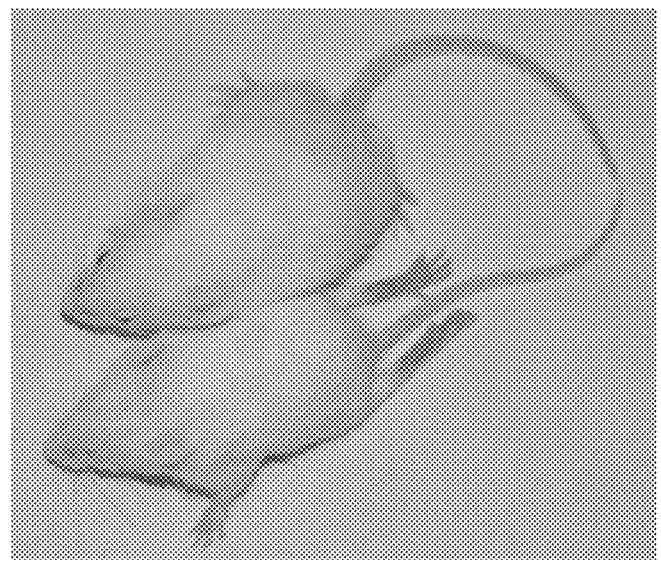
FIG. 2 compares symptoms of EV71-infected mice treated with Compound 1.

Experimental Example 3: Therapeutic Effect of Compound 1 on EV71-Infected Mice 10-day-old SPF grade ICR mice (female:male 1:1) were used. A placebo group and a treatment group with Compound 1 were set, each group having 10 mice. The mice were infected with the virus by intraperitoneal injection. 2 hrs after infection, the mice were administered by intraperitoneal injection. The dosage of Compound 1 was set to 1 mg/kg body weight/day. The mice in the placebo group were injected with the same dose of normal saline, and the mice in each group were administered once a day for consecutive 7 days. From the day of virus infection, the observation was made twice a day for 14 days. The weight, symptoms and survival rate of the mice were recorded. The results show that the mortality rate of mice treated with Compound 1 is reduced to 40%, and the mortality rate of mice in the placebo group is 100% (FIG. 1). Also, the mice in the treatment group have reduced symptoms, and significantly alleviated weight loss and paralysis, and the surviving mice recover to normal after 14 days (FIG. 2).

PHARMACOKINETIC EXPERIMENT

Experimental Example 1: Pharmacokinetic Experiment of Compound 6 in Plasma

Male ICR mice weighing 20-22 g were intraperitoneally injected with Compound 6 (1.5 mg/kg), and then blood was taken from the orbit at 5 min, 10 min, 15 min, 30 min, 1 h, 2 h, 4 h, 6 h, 8 h, 12 h, and 24 h. The heparin anticoagulant was added, placed on ice, and centrifuged at 7000 r/min for 7 min. The plasma was separated for use. 60 μl of acetonitrile was added to 20 μL of the plasma sample obtained after administration, to precipitate the protein. After high-speed centrifugation at 13300 r/min for 7 min, 60 μl of the supernatant was taken and centrifuged at 13300 r/min for 4 min. 5 μl of the supernatant was taken for UPLC/MS analysis. Plasma pharmacokinetics was analyzed by Winnolin software and fitted by a non-compartmental model. The pharmacokinetic parameters are shown in Table 3.

TABLE 3

Non-compartmental model parameters in plasma pharmacokinetics of metabolite of Compound 6

| Statistical moment parameter | Unit | 1 | 2 | 3 | Mean ± SD |
|---|---|---|---|---|---|
| AUC(0-t) | h*ng/ml | 254.531 | 286.742 | 276.263 | 272.51 ± 16.43 |
| AUC(0-∞) | h*ng/ml | 408.575 | 352.686 | 397.912 | 386.39 ± 29.67 |
| MRT(0-t) | h | 5.977 | 4.964 | 4.555 | 5.17 ± 0.73 |
| MRT(0-∞) | h | 26.762 | 12.384 | 22.354 | 20.5 ± 7.37 |
| t1/2z | h | 25.719 | 14.311 | 26.875 | 22.3 ± 6.94 |
| Tmax | h | 0.250 | 0.083 | 0.167 | 0.17 ± 0.08 |
| Cmax | ng/ml | 261 | 340 | 331 | 310.67 ± 43.25 |

Experimental Example 2: Pharmacokinetic Experiment of Compound 20 in Plasma

Male ICR mice weighing 20-22 g were intraperitoneally injected with Compound 20 (1.5 mg/kg), and then blood was taken from the orbit at 5 min, 10 min, 15 min, 30 min, 1 h, 2 h, 4 h, 6 h, 8 h, 12 h, and 24 h. The heparin anticoagulant was added, placed on ice, and centrifuged at 7000 r/min for 7 min. The plasma was separated for use. 60 μl of acetonitrile was added to 20 μL of the plasma sample obtained after administration, to precipitate the protein. After high-speed centrifugation at 13300 r/min for 7 min, 60 μl of the supernatant was taken and centrifuged at 13300 r/min for 4 min. 5 μl of the supernatant was taken for UPLC/MS analysis. Plasma pharmacokinetics was analyzed by Winnolin software and fitted by a non-compartmental model. The pharmacokinetic parameters are shown in Table 4.

TABLE 4

Non-compartmental model parameters in plasma pharmacokinetics of metabolite of Compound 20

| Statistical moment parameter | Unit | 1 | 2 | 3 | Mean ± SD |
|---|---|---|---|---|---|
| AUC(0-t) | h*ng/ml | 511.465 | 491.887 | 470.648 | 491.33 ± 20.41 |
| AUC(0-∞) | h*ng/ml | 822.583 | 646.948 | 542.953 | 670.83 ± 141.33 |
| MRT(0-t) | h | 8.851 | 8.384 | 8.741 | 8.66 ± 0.24 |
| MRT(0-∞) | h | 25.021 | 16.409 | 12.279 | 17.90 ± 6.50 |

TABLE 4-continued

Non-compartmental model parameters in plasma pharmacokinetics of metabolite of Compound 20

| Statistical moment parameter | Unit | 1 | 2 | 3 | Mean ± SD |
|---|---|---|---|---|---|
| $t_{1/2z}$ | h | 19.133 | 12.385 | 7.838 | 13.12 ± 5.68 |
| $T_{max}$ | h | 0.167 | 0.083 | 0.083 | 0.11 ± 0.05 |
| $C_{max}$ | ng/ml | 228 | 283 | 342 | 284.33 ± 57.01 |

TOXICOLOGICAL EXPERIMENT

Experimental Example 1: Toxicity Test of Compound 6 in ICR Mice after Single Administration by Intraperitoneal Injection 22 10-day-old ICR mice were randomly assigned to 17 groups, and given Compound 6 once by intraperitoneal injection at a dosage of 0.625, 1.25, 2.5, 5, 10, 20, 40, 80, 100, 160, 200, 250, 300, 470, 500, 1000, or 2000 mg/kg. 1-2 animals were included in each group, and the male and female mice were administered alternately. The symptoms of poisoning, the time when the symptoms of poisoning appeared, the degree exhibited, the development process, the characteristics before the death of the animals and the time of death were observed for 14 days. The dead animals are necropsied and the changes in main organs were observed. On day 1 after administration, the weight of the animals in the 160 mg/kg group is decreases by 0.3 g, and the weight of the animals in the 0.625, 1.25, 2.5, 5, 10, 20, 40, 80, 100 mg/kg group is increased, compared to the day of administration. See Table 5 for details. Under the conditions in this experiment, ICR mice were given Compound 6 once by intraperitoneal injection. The minimum lethal dose was 200 mg/kg and the maximum tolerated dose was 160 mg/kg.

TABLE 5

Changes in body weight of ICR mice in toxicity test of Compound 6 after single administration by intraperitoneal injection

| Dose mg/kg | Gender | Weight before administration | Weight on day 1 after administration | Changes in body weight |
|---|---|---|---|---|
| 0.625 | Female | 6.7 | 7.3 | Increase |
| 1.25 | Female | 6.7 | 7.1 | Increase |
| 1.25 | Male | 6.7 | 7.2 | Increase |
| 2.5 | Female | 6.9 | 7.5 | Increase |
| 2.5 | Male | 6.4 | 7 | Increase |
| 5 | Male | 6.4 | 6.9 | Increase |
| 10 | Male | 5.8 | 6.5 | Increase |
| 20 | Female | 6.5 | 7.5 | Increase |
| 40 | Male | 7.3 | 7.7 | Increase |
| 80 | Female | 6.6 | 7.3 | Increase |
| 100 | Female | 7.1 | 7.3 | Increase |
| 160 | Female | 6.6 | 6.3 | Decrease |

Experimental Example 2: Toxicity Test of Compound 20 in ICR Mice after Single Administration by Intraperitoneal Injection 24 10-day-old ICR mice were randomly assigned to 19 groups, and given Compound 6 once by intraperitoneal injection at a dosage of 0.625, 1.25, 2.5, 5, 10, 20, 40, 60, 80, 100, 120, 136, 160, 270, 320, 500, 690, 1000, or 2000 mg/kg. 1-2 animals were included in each group, and the male and female mice were administered alternately. The symptoms of poisoning, the time when the symptoms of poisoning appeared, the degree exhibited, the development process, the characteristics before the death of the animals and the time of death were observed for 14 days. The dead animals are necropsied and the changes in main organs were observed. On day 1 after administration, the weight of the animals in the 80-136 mg/kg group has no change or is decreases by 0.2-0.3 g, and the weight of the animals in the 0.625, 1.25, 2.5, 5, 10, 20, 40, or 80 mg/kg group is increased, compared to the day of administration. See Table 6 for details. Under the conditions in this experiment, ICR mice were given Compound 20 once by intraperitoneal injection. The minimum lethal dose was 160 mg/kg and the maximum tolerated dose was 136 mg/kg.

TABLE 6

Changes in body weight of ICR mice in toxicity test of Compound 20 after single administration by intraperitoneal injection

| Dose mg/kg | Gender | Weight before administration | Weight on day 1 after administration | Changes in body weight |
|---|---|---|---|---|
| 0.625 | Female | 4.6 | 5.2 | Increase |
| 1.25 | Male | 5.8 | 6.6 | Increase |
| 2.5 | Female | 6.2 | 6.8 | Increase |
| 2.5 | Male | 6.2 | 6.7 | Increase |
| 5 | Female | 5.8 | 6.4 | Increase |
| 10 | Male | 5.6 | 6.5 | Increase |
| 20 | Female | 5.8 | 5.9 | Increase |
| 40 | Male | 6.2 | 6.8 | Increase |
| 60 | Female | 6.8 | 7 | Increase |
| 80 | Female | 5.1 | 4.8 | Decrease |
| 80 | Male | 6.4 | 6.4 | No change |
| 100 | Male | 6.8 | 6.8 | No change |
| 120 | Female | 7 | 6.8 | Decrease |
| 120 | Male | 6.9 | 6.9 | No change |
| 136 | Male | 7 | 6.7 | Decrease |

Experimental Example 3: Test of Reverse Mutation in Histidine-Deficient *Salmonella typhimurium* Induced by Compound 6

The mutagenic effect of Compound 6 on the strains TA100 and TA102 was detected by determining the reverse mutation in histidine-deficient *Salmonella typhimurium* by pre-loaded culture dish method. The dosage of Compound 6 is 8, 40, 200, 1000, or 5000 μg/dish under activated and non-activated conditions, and the mutagenic effects on TA100 and TA102 were tested. Under the conditions in this example, Compound 6 shows no significant mutagenic effects on TA100 and TA102 at a concentration in the range of 8-5000 μg/dish, under both activated and non-activated conditions, and the results were negative, as shown in Table 7.

TABLE 7

Test of reverse mutation in histidine-deficient *Salmonella typhimurium* induced by Compound 6

| Dose (μg/dish) | Number of colonies | | | |
|---|---|---|---|---|
| | TA100(−S9) | TA100(+S9) | TA102(−S9) | TA102(+S9) |
| Blank control | 178.3 ± 5.0 | 200.3 ± 11.0 | 226.0 ± 5.4 | 243.8 ± 7.0 |
| Solvent control | 165.3 ± 10.7 | 170.7 ± 10.9 | 225.0 ± 7.5 | 236.5 ± 5.0 |
| 8 | 152.7 ± 9.4 | 159.3 ± 11.3 | 223.0 ± 9.1 | 235.0 ± 9.6 |
| 40 | 141.8 ± 5.9 | 158.7 ± 10.7 | 205.0 ± 14.6 | 222.5 ± 9.3 |
| 200 | 152.7 ± 9.5 | 158.5 ± 11.5 | 192.8 ± 18.6 | 208.3 ± 6.8 |
| 1000 | 113.0 ± 14.2 | 127.7 ± 10.1 | 182.3 ± 10.3 | 195.2 ± 8.6 |
| 5000 | 110.5 ± 7.8 | 114.7 ± 3.8 | 147.2 ± 20.3 | 180.7 ± 11.7 |
| 1.5 (NaN3) | >1000 | — | — | — |
| 1.0 (MMC) | — | — | >1000 | — |
| 60.0 (2-AF) | — | >1000 | — | >1000 |

What is claimed is:

1. A lycorine derivative of General Formula (I), or a pharmaceutically acceptable salt thereof:

General Formula (I)

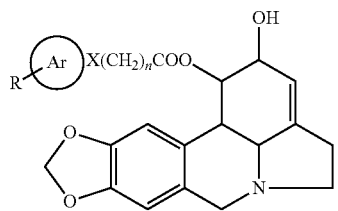

wherein X is O, S or $CH_2$; n=0, 1, 2, 3, 4, or 5; Ar is a C6-10 aromatic ring or a C3-10 heteroaromatic ring; R is optionally mono-substituted, di-substituted or multi-substituted, and R is independently selected from hydrogen, halogen, nitro, amino, hydroxy, C1-6 alkyl, C1-6 alkoxy, C1-6 alkylamino, C6-10 aryl, C1-6 alkynyl, C1-6 alkenyl, C3-6 cycloalkyl, C3-6 heterocycloalkyl, C1-6 alkylacyl, and C6-10 arylacyl, where the C3-10 heteroaromatic ring contains a heteroatom, and the heteroatom is selected from N, O, and S.

2. The lycorine derivative of General Formula (I) according to claim 1, or a pharmaceutically acceptable salt thereof, wherein Ar is selected from phenyl, naphthyl, pyrimidinyl, pyridinyl, furyl, thienyl, pyrrolyl, isoxazolyl, isothiazolyl, pyrazolyl, oxazolyl, thiazolyl, imidazolyl, pyridazinyl, pyrazinyl, benzofuryl, benzothienyl, indolyl, quinolinyl, isoquinolinyl, purinyl, benzoxazolyl, and benzothiazolyl; and R is selected from hydrogen, F, Cl, Br, I, nitro, amino, hydroxyl, C1-4 alkyl, C1-4 alkoxy, C1-4 alkylamino, phenyl, C1-4 alkynyl, and C1-4 alkenyl.

3. The lycorine derivative of General Formula (I) according to claim 2, or a pharmaceutically acceptable salt thereof, wherein the occurrence of substitution with the substituent R on the phenyl group is at the para, meta, or ortho position; and R is optionally mono-substituted, di-substituted or multi-substituted.

4. The lycorine derivative of General Formula (I) according to claim 1, or a pharmaceutically acceptable salt thereof, wherein the compound is selected from:

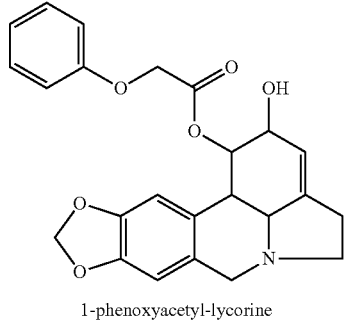

1-phenoxyacetyl-lycorine

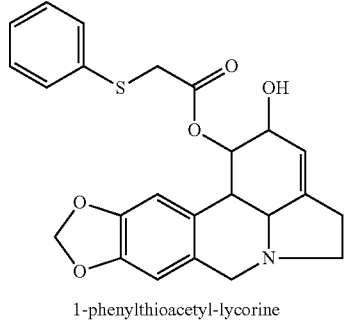

1-phenylthioacetyl-lycorine

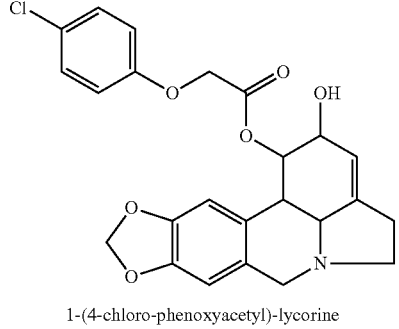

1-(4-chloro-phenoxyacetyl)-lycorine

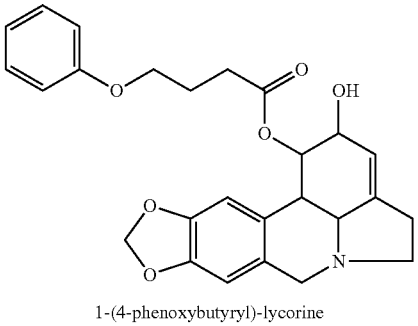

1-(4-phenoxybutyryl)-lycorine

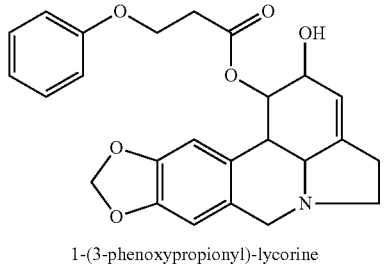

1-(3-phenoxypropionyl)-lycorine

-continued
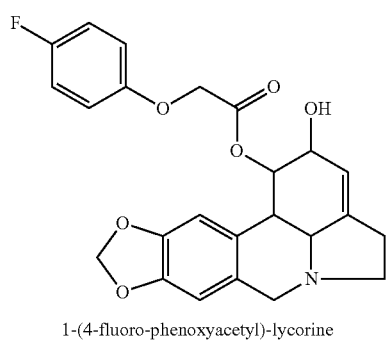
1-(4-fluoro-phenoxyacetyl)-lycorine (6)
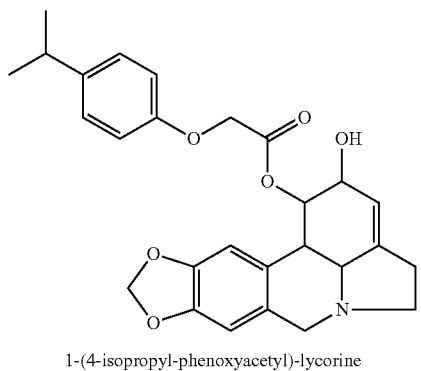
1-(4-isopropyl-phenoxyacetyl)-lycorine (10)
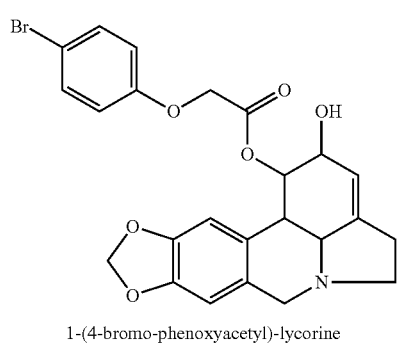
1-(4-bromo-phenoxyacetyl)-lycorine (7)
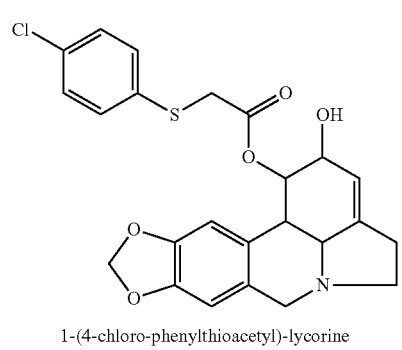
1-(4-chloro-phenylthioacetyl)-lycorine (11)
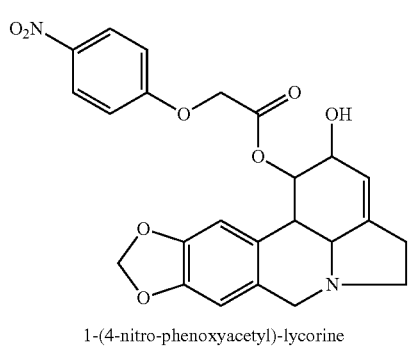
1-(4-nitro-phenoxyacetyl)-lycorine (8)
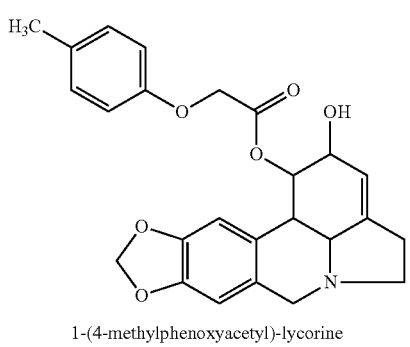
1-(4-methylphenoxyacetyl)-lycorine (12)
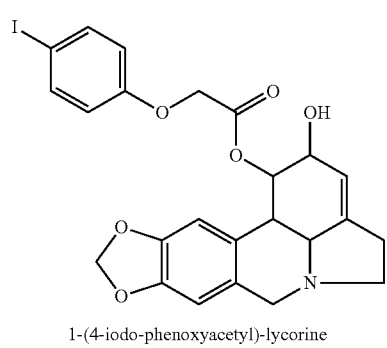
1-(4-iodo-phenoxyacetyl)-lycorine (9)
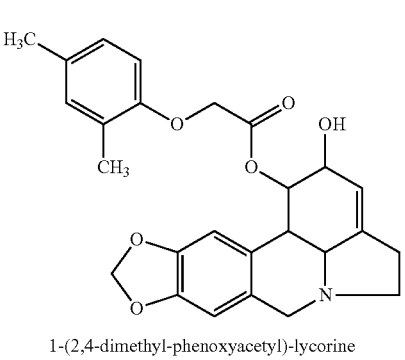
1-(2,4-dimethyl-phenoxyacetyl)-lycorine (13)

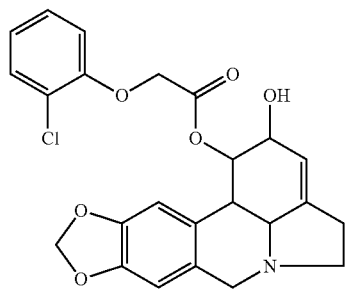
1-(2-chloro-phenoxyacetyl)-lycorine (14)
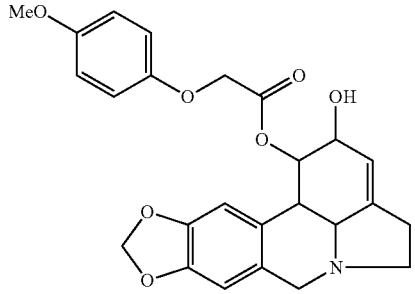
1-(4-methoxy-phenoxyacetyl)-lycorine (18)
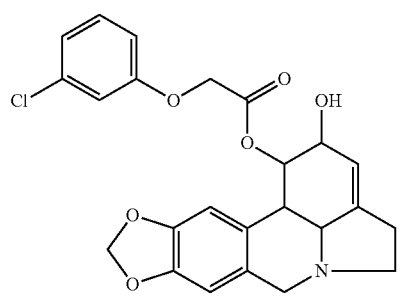
1-(3-chloro-phenoxyacetyl)-lycorine (15)
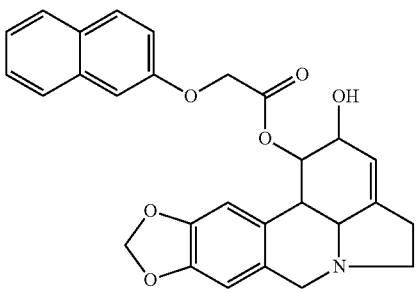
1-(2-naphthyl-phenoxyacetyl)-lycorine (19)
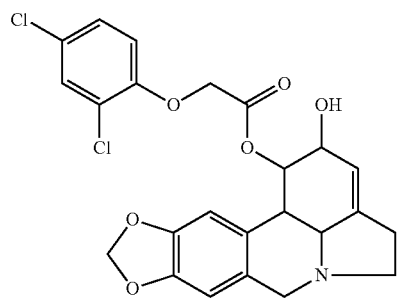
1-(2,4-dichloro-phenoxyacetyl)-lycorine (16)
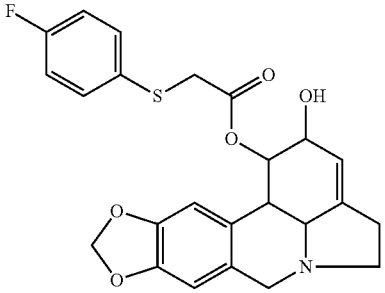
1-(4-fluoro-phenylthioacetyl)-lycorine (20)
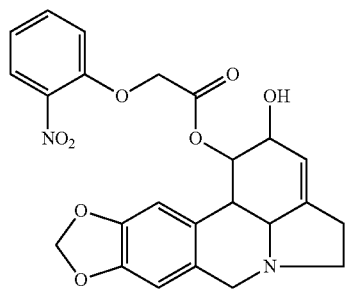
1-(4-nitro-phenoxyacetyl)-lycorine (17)
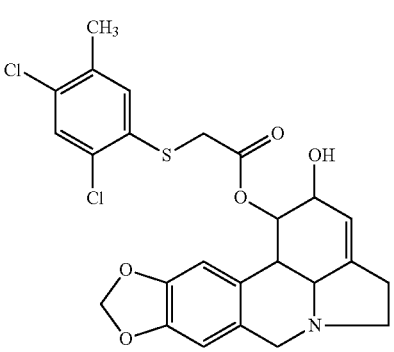
1-(2,4-dichloro-5-methyl-phenylthioacetyl)-lycorine (21)

-continued
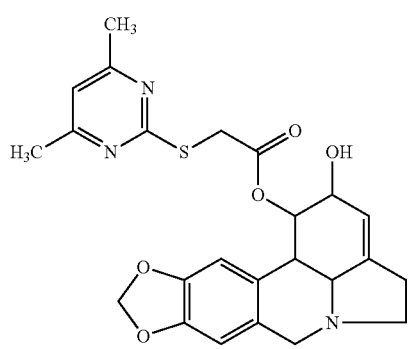
1-[2-(4,6-dimethyl-pyrmidinyl)thioacetyl]-lycorine (22)
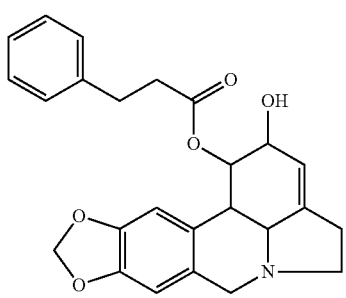
1-(3-phenylpropionyl)-lycorine (23)
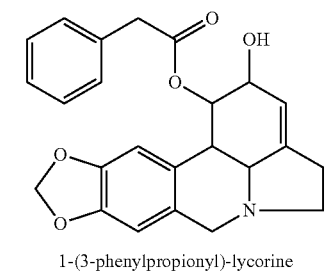
1-(3-phenylpropionyl)-lycorine (24)
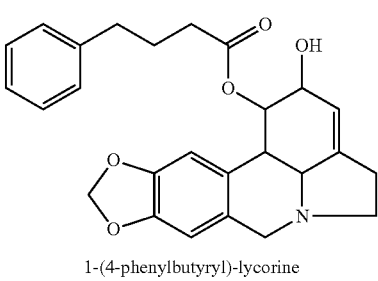
1-(4-phenylbutyryl)-lycorine (25)
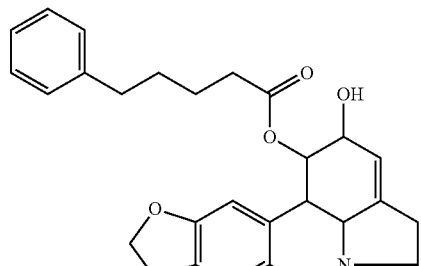
1-(5-phenylvaleryl)-lycorine (26)
-continued
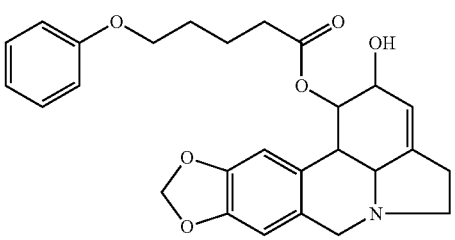
1-[3-(2-pyridinyl)propionyl]-lycorine (27)
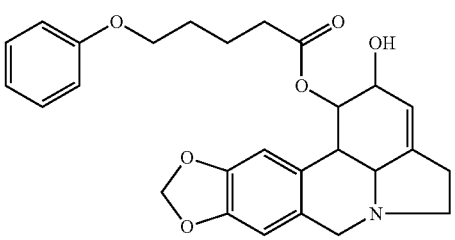
1-(5-phenoxyvaleryl)-lycorine (28)
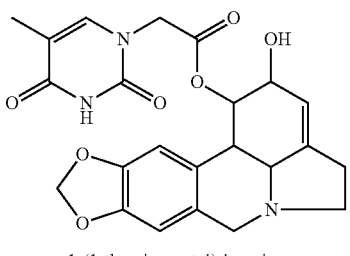
1-(1-thymineacetyl)-lycorine (29)
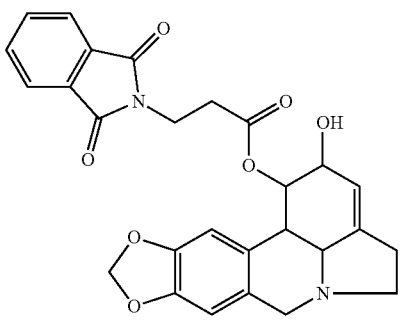
1-(3-phthalimidopropionyl)-lycorine (30)

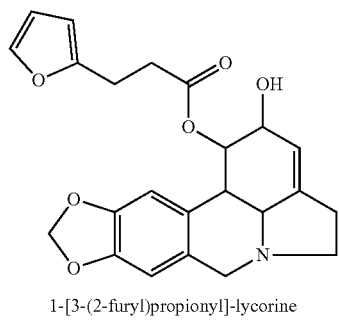

1-[3-(2-furyl)propionyl]-lycorine (31)

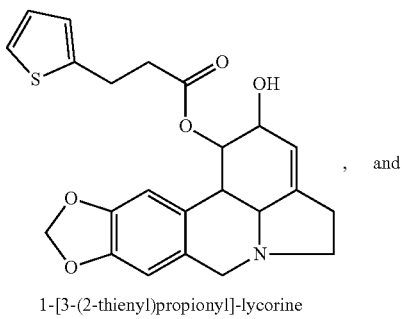

1-[3-(2-thienyl)propionyl]-lycorine (32) , and

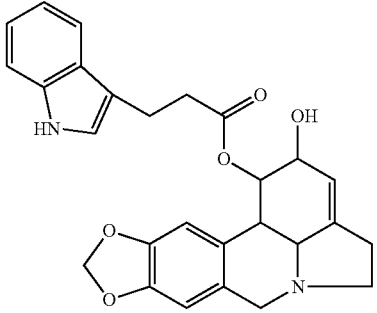

1-[3-(3-indolyl)propionyl]-lycorine (33)

5. A pharmaceutical composition, comprising a lycorine derivative according to claim 1 or a pharmaceutically acceptable salt thereof, and a pharmaceutically acceptable carrier or excipient.

6. The pharmaceutical composition according to claim 5, wherein the pharmaceutical composition is selected from tablets, capsules, pills, and injections.

7. The pharmaceutical composition according to claim 5, wherein the pharmaceutical composition is selected from controlled-release dosage forms, sustained-release dosage forms, and various particulate delivery systems.

8. A method for treating a disease caused by a virus, the method comprising administering a lycorine derivative according to claim 1 or a pharmaceutically acceptable salt thereof to a subject in need thereof.

9. The method according to claim 8, wherein the virus is Enterovirus 71 (EV71) or Coxsackievirus A16 (CA16).

10. The method according to claim 8, wherein the disease is hand-foot-mouth disease.

* * * * *